(12) United States Patent
Rogers et al.

(10) Patent No.: US 8,871,189 B2
(45) Date of Patent: Oct. 28, 2014

(54) MMP-TARGETED THERAPEUTIC AND/OR DIAGNOSTIC NANOCARRIERS

(71) Applicant: Mallinckrodt LLC, Hazelwood, MO (US)

(72) Inventors: Thomas E. Rogers, Ballwin, MO (US); John N. Freskos, Clayton, MO (US)

(73) Assignee: Mallinckrodt LLC, Hazelwood, MO (US)

(*) Notice: Subject to any disclaimer, the term of this patent is extended or adjusted under 35 U.S.C. 154(b) by 0 days.

(21) Appl. No.: 13/689,694

(22) Filed: Nov. 29, 2012

(65) Prior Publication Data

US 2013/0183236 A1 Jul. 18, 2013

Related U.S. Application Data

(60) Provisional application No. 61/565,461, filed on Nov. 30, 2011.

(51) Int. Cl.
| | | |
|---|---|---|
| *A61K 31/74* | (2006.01) | |
| *A61K 47/48* | (2006.01) | |
| *A61K 49/08* | (2006.01) | |
| *A61K 49/00* | (2006.01) | |
| *A61K 51/04* | (2006.01) | |
| *A61K 49/04* | (2006.01) | |
| *B82Y 5/00* | (2011.01) | |

(52) U.S. Cl.
CPC ....... *A61K 51/0497* (2013.01); *A61K 47/48815* (2013.01); *A61K 49/085* (2013.01); *A61K 49/00* (2013.01); *A61K 47/48215* (2013.01); *A61K 47/48061* (2013.01); *A61K 49/04* (2013.01); *B82Y 5/00* (2013.01)
USPC ...................................................... 424/78.17

(58) Field of Classification Search
None
See application file for complete search history.

(56) References Cited

U.S. PATENT DOCUMENTS

| | | | | |
|---|---|---|---|---|
| 5,225,181 | A * | 7/1993 | Srivastava et al. | 530/391.3 |
| 8,003,105 | B2 * | 8/2011 | Nakahara et al. | 424/155.1 |
| 2006/0210549 | A1 | 9/2006 | Srivastava et al. | |
| 2009/0022782 | A1 | 1/2009 | Akita et al. | |
| 2009/0246142 | A1 | 10/2009 | Bhatia et al. | |
| 2010/0041773 | A1 | 2/2010 | Peterson | |

FOREIGN PATENT DOCUMENTS

| | | | |
|---|---|---|---|
| WO | 02/076491 | A1 | 10/2002 |
| WO | 2005/037862 | A1 | 4/2005 |
| WO | 2010/012473 | A2 | 2/2010 |
| WO | 2010/117957 | A2 | 10/2010 |
| WO | 2011/008992 | A2 | 1/2011 |
| WO | WO 2011139343 | A2 * | 11/2011 |

OTHER PUBLICATIONS

Becker et al., "Orally Active MMP-1 Sparing α-Tetrahydropyanyl and α-Piperidinyl Sulfone Matrix Metalloproteinase (MMP) Inhibitors with Efficacy in Cancer, Arthritis, and Cardiovascular Disease," J. Med. Chem. 2010, vol. 53, pp. 6653-6680.
Chau et al., Bioconjugate Chem., 2004, vol. 15, 931-941.
Matter, "Tumor Angiogenesis as a Therapeutic Target," Drug Discovery Today, 2001, vol. 6, 1005-1024.
Zhu et al., Theranostics, 2011, vol. 1, 18-27.
International Search Report and Written Opinion, Mailing date Feb. 28, 2013, PCT Application No. PCT/US2012/067236, 12 pages.

* cited by examiner

*Primary Examiner* — Paul Dickinson

(57) ABSTRACT

The present invention provides targeted delivery compositions and methods of using the compositions for treating and diagnosing a disease state in a subject.

35 Claims, 10 Drawing Sheets

Conjugate 1

A

B

A

B

MMP-TARGETED THERAPEUTIC AND/OR DIAGNOSTIC NANOCARRIERS

CROSS-REFERENCES TO RELATED APPLICATIONS

The present application claims priority to U.S. Provisional Patent Application No. 61/565,461, filed Nov. 30, 2011, the entirety of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Cancer is a class of diseases that can affect people of all ages. Accordingly, there is considerable effort to provide therapies that can treat or diagnose cancer in patients. Targeted delivery of nanocarriers in the body has been discussed recently as a potential new avenue in drug delivery and diagnostic imaging techniques. Unfortunately, obstacles still exist in making nanocarrier based-products that can effectively treat or diagnose cancer.

Many if not all solid tumors either express matrix metalloproteinase (MMP) enzymes on their surface or excrete it into the surrounding matrix or cause MMP enzymes to be produced via angiogenesis (see, Y. Chau, F. E. Tan, and R. Langer, *Bioconjugate Chem*, 2004, 15:931-941 and A. Matter, 'Tumor Angiogenesis as a Therapeutic Target', DRUG DISCOVERY TODAY, 6:1005-1024 (2001)). Thus, the tumor environment is particularly rich in MMP 2, 9, and 13 enzyme content as well as others, such as members of the membrane bound family, MMP 14-17. The activity of MMP enzymes in a mouse tumor model has been exquisitely revealed by use of a FRET-based MMP enzyme assay where fluorescent dye is released in vivo once the dye-bearing molecule is transported into the tumor (L. Zhu, J. Xie, M. Swierczewska, F. Zhang, Q. Quan, Y. Ma, X. Fang, K. Kim, S. Lee, X. Chen, *Theranostics*, 2011, 1:18-27).

Nanoparticles, such as liposomes, are commonly modified to incorporate polyethylene glycol (PEG) groups on their surface to enhance in vivo performance. It would be advantageous to target the liposomal nanoparticle to a tumor cell related receptor or enzyme within the tumor and also have it targeted for cellular uptake of the cytotoxic payload (or other cargo) by endocytosis (or other internalization mechanism) driven by enzyme/receptor recognition and binding events.

There remains a need for new targeted delivery approaches that can treat or diagnose cancer and provide ways to facilitate personalized care for a patient. The present disclosure addresses this need.

BRIEF SUMMARY OF THE INVENTION

The present invention provides targeted delivery compositions and their methods of use in treating and diagnosing a disease state, such as a cancerous condition, in a subject.

In one aspect of the invention, the targeted delivery compositions can include a nanocarrier including a therapeutic agent, a diagnostic agent, or a combination thereof, and a conjugate having the formula:

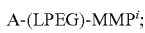

wherein,
A is an attachment component for attaching said conjugate to said nanocarrier;
(LPEG) is a linking group selected from a linear assembly of from 1 to 3 polyethylene glycol components; an [(EG)(P)]$_m$ linking group as defined herein; and a —$Z^1$—$Z^2$—$Z^3$— linking group as defined herein; and
MMP$^i$ is a MMP inhibitor.

The targeted delivery compositions and methods of making and using such compositions provide a number of unique advantages to the areas of drug delivery and diagnostic imaging. For example, the targeted delivery compositions linking groups can be synthesized to have a discrete number of monomers, which can be tailored to, e.g., provide a specific length and/or chemical property. Furthermore, the linking groups are fully customizable and can be prepared to include only one type of monomer or multiple types of monomers in any order. The linking groups can also be synthesized on a solid phase support, which allows for simple, automated syntheses. In addition to the linking groups, the targeted delivery compositions can be used to treat diseases more effectively by utilizing lower doses of agents that if administered with normal dosage amounts might otherwise be toxic to a patient.

A further understanding of the nature and advantages of the present invention can be realized by reference to the remaining portions of the specification and the drawings.

DETAILED DESCRIPTION OF THE INVENTION

I. Definitions

Figure 1:
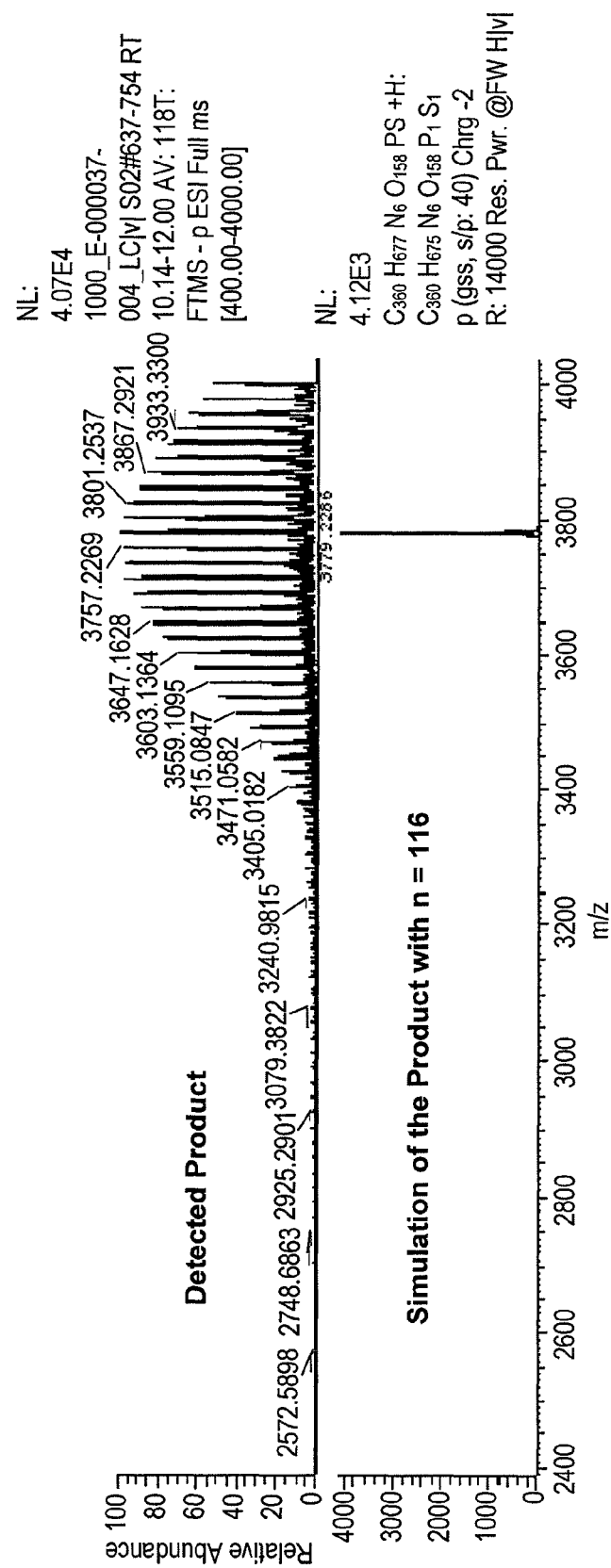
FIG. 1 shows a mass spectrum for Conjugate 1.
Figure 2:
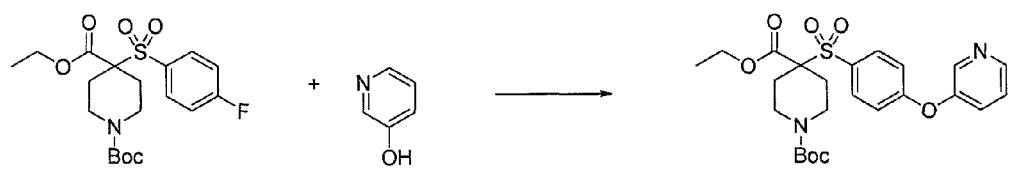
FIG. 2 shows the synthesis of 1-tert-butyl 4-ethyl 4-(4-(pyridin-3-yloxy)phenylsulfonyl)piperidine-1,4-dicarboxylate.

As used herein, the term "targeted delivery composition" refers to a composition of a nanocarrier attached to a conjugate having the formula: A-(LPEG)-MMP$^i$, as further described herein. The compositions of the present invention can be used as therapeutic compositions, as diagnostic compositions, or as both therapeutic and diagnostic compositions. In certain embodiments, the compositions can be targeted to a specific MMP-expressing tissue within a subject or a test sample, as described further herein.

As used herein, the term "nanocarrier" refers to particles of varied size, shape, type and use, which are further described herein. As will be appreciated by one of ordinary skill in the art, the characteristics of the nanocarriers, e.g., size, can depend on the type and/or use of the nanocarrier as well as other factors generally well known in the art. In general, nanocarriers can range in size from about 1 nm to about 1000 nm. In other embodiments, nanocarriers can range in size from about 10 nm to about 200 nm. In yet other embodiments, nanocarriers can range in size from about 50 nm to about 150 nm. In certain embodiments, the nanocarriers are greater in size than the renal excretion limit, e.g., greater than about 6 nm in diameter. In other embodiments, the nanocarriers are small enough to avoid clearance from the bloodstream by the liver, e.g., smaller than 1000 nm in diameter. Nanocarriers can include spheres, cones, spheroids and other shapes generally known in the art. Nanocarriers can be hollow (e.g., solid outer core with a hollow inner core) or solid or be multilayered with hollow and solid layers or a variety of solid layers. For example, a nanocarrier can include a solid core region and a solid outer encapsulating region, both of which can be cross-linked. Nanocarriers can be composed of one substance or any combination of a variety of substances, including lipids, polymers, silica, magnetic materials, or metallic materials, such as gold, iron oxide, and the like. Lipids can include fats, waxes, sterols, cholesterol, fat-soluble vitamins, monoglycerides, diglycerides, phospholipids, sphingolipids, glycolipids, cationic or anionic lipids, derivatized lipids, cardiolipin and the like. Polymers can include block copolymers generally, poly(lactic acid), poly(lactic-co-glycolic acid), polyethylene glycol, acrylic polymers, cationic polymers, as well as other polymers known in the art for use in making nanocarriers. In some embodiments, the polymers can be biodegradable and/or biocompatible. Nanocarriers can include a liposome, a micelle, a lipoprotein, a lipid-coated bubble, a block copolymer micelle, a polymersome, a niosome, a quantum dot, an iron oxide particle, a gold particle, a dendrimer, or a silica particle. In certain embodiments, a lipid monolayer or bilayer can fully or partially coat a nanocarrier composed of a material capable of being coated by lipids, e.g., polymer nanocarriers. In some embodiments, liposomes can include multilamellar vesicles (MLV), large unilamellar vesicles (LUV), and small unilamellar vesicles (SUV).

As used herein, the term "therapeutic agent" refers to a compound or molecule that, when present in an effective amount, produces a desired therapeutic effect on a subject in need thereof. The present invention contemplates a broad range of therapeutic agents and their use in conjunction with the targeted delivery compositions, as further described herein.

As used herein, the term "diagnostic agent" refers to a component that can be detected in a subject or test sample and is further described herein.

As used herein, the term "conjugate" refers generally to a molecule that includes a linking group. In some embodiments, a conjugate of the present invention has the formula: A-(LPEG)-MMP$^i$. A is an attachment component that can attach (covalently or non-covalently) the conjugate to a nanocarrier. The conjugate can be covalently bonded to any part of a nanocarrier including the surface or an internal region. Covalent attachment can be achieved through a functional group using a linking chemistry well known in the art, which is further described herein. In other embodiments, a non-covalent attachment can include interactions that are generally well known in the art and further described herein. The conjugates of the present invention can further include a linking group having the formula (LPEG) and a targeting agent, MMP$^i$, each being described further herein.

As used herein, the term "linking group" refers to part of a conjugate that links two components, e.g., an attachment component and a targeting agent. Depending on the conjugate being prepared and the properties desired for the conjugate, the linking group can be assembled from readily available monomeric components to achieve an appropriate separation of targeting agent and nanocarrier or agent.

As used herein, the term "targeting agent" refers to a molecule that is specific for a target, such as a matrix metalloproteinase (MMP). In certain embodiments, a targeting agent can include a small molecule mimic or inhibitor of the target enzyme. MMP inhibitors (MMP$^i$) can bind a wide variety of MMPs, including targets in organs, tissues, cells, extracellular matrix components, and/or intracellular compartments that can be associated with a specific developmental stage of a disease. In some embodiments, targets can include cancer cells, particularly cancer stem cells. Targets can further include antigens on a surface of a cell, or a tumor marker that is an antigen present or more prevalent on a cancer cell as compared to normal tissue.

As used herein, the term "stealth agent" refers to a molecule that can modify the surface properties of a nanocarrier. A stealth agent can prevent nanocarriers from sticking to each other and to blood cells or vascular walls. In certain embodiments, stealth nanocarriers, e.g., stealth liposomes, can reduce immunogenicity and/or reactogenicity when the nanocarriers are administered to a subject. Stealth agents can also increase blood circulation time of a nanocarrier within a subject. In some embodiments, a nanocarrier can include a stealth agent such that, for example, the nanocarrier is partially or fully composed of a stealth agent or the nanocarrier is coated with a stealth agent. Stealth agents for use in the present invention can include those generally well known in the art. In certain embodiments, a stealth agent can include "polyethylene glycol," which is well known in the art and refers generally to an oligomer or polymer of ethylene oxide. Polyethylene glycol (PEG) can be linear or branched, wherein branched PEG molecules can have additional PEG molecules emanating from a central core and/or multiple PEG molecules can be grafted to the polymer backbone. PEG can include low or high molecular weight PEG, e.g., PEG500, PEG2000, PEG3400, PEG5000, PEG6000, PEG9000, PEG10000, PEG20000, or PEG50000 wherein the number, e.g., 500, indicates the average molecular weight. In certain embodiments, PEGylated-lipids are present in a bilayer of the nanocarrier, e.g., a liposome, in an amount sufficient to make the nanocarrier "stealth," wherein a stealth nanocarrier shows reduced immunogenicity. Other suitable stealth agents can include but are not limited to dendrimers, polyalkylene oxide, polyvinyl alcohol, polycarboxylate, polysaccharides, and/or hydroxyalkyl starch. Stealth agents can be attached to the targeted delivery compositions of the present invention through covalent and/or non-covalent attachment, as described further herein.

As used herein, the term "embedded in" refers to the location of an agent on or in the vicinity of the surface of a nanocarrier. Agents embedded in a nanocarrier can, for example, be located within a bilayer membrane of a liposome or located within an outer polymer shell of a nanocarrier so as to be contained within that shell.

As used herein, the term "encapsulated in" refers to the location of an agent that is enclosed or completely contained within the inside of a nanocarrier. For liposomes, for example, therapeutic and/or diagnostic agents can be encapsulated so as to be present in the aqueous interior of the liposome. Release of such encapsulated agents can then be triggered by certain conditions intended to destabilize the liposome or otherwise effect release of the encapsulated agents.

As used herein, the term "tethered to" refers to attachment of one component to another component so that one or more of the components has freedom to move about in space. In certain exemplary embodiments, an attachment component can be tethered to a nanocarrier so as to freely move about in solution surrounding the nanocarrier. In some embodiments, an attachment component can be tethered to the surface of a nanocarrier, extending away from the surface.

As used herein, the term "lipid" refers to lipid molecules that can include fats, waxes, sterols, cholesterol, fat-soluble vitamins, monoglycerides, diglycerides, phospholipids, sphingolipids, glycolipids, cationic or anionic lipids, derivatized lipids, and the like. Lipids can form micelles, monolayers, and bilayer membranes. In certain embodiments, the lipids can self-assemble into liposomes. In other embodiments, the lipids can coat a surface of a nanocarrier as a monolayer or a bilayer.

As used herein, the term "subject" refers to any mammal, in particular human, at any stage of life.

As used herein, the terms "administer," "administered," or "administering" refers to methods of administering the targeted delivery compositions of the present invention. The targeted delivery compositions of the present invention can be administered in a variety of ways, including topically, parenterally, intravenously, intradermally, intramuscularly, colonically, rectally or intraperitoneally. Parenteral administration and intravenous administration are the preferred methods of administration. The targeted delivery compositions can also be administered as part of a composition or formulation.

As used herein, the terms "treating" or "treatment" of a condition, disease, disorder, or syndrome includes (i) inhibiting the disease, disorder, or syndrome, i.e., arresting its development; and (ii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, the term "formulation" refers to a mixture of components for administration to a subject. Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. The formulations of a targeted delivery composition can be presented in unit-dose or multi-dose sealed containers, such as ampoules and vials. A targeted delivery composition, alone or in combination with other suitable components, can be made into aerosol formulations (i.e., they can be "nebulized") to be administered via inhalation through the mouth or the nose. Aerosol formulations can be placed into pressurized acceptable propellants, such as dichlorodifluoromethane, propane, nitrogen, and the like. Suitable formulations for rectal administration include, for example, suppositories, which comprise an effective amount of a targeted delivery composition with a suppository base. Suitable suppository bases include natural or synthetic triglycerides or paraffin hydrocarbons. In addition, it is also possible to use gelatin rectal capsules which contain a combination of the targeted delivery composition with a base, including, for example, liquid triglycerides, polyethylene glycols, and paraffin hydrocarbons. In certain embodiments, formulations can be administered topically or in the form of eye drops.

Embodiments of the Invention

II. General

The present invention provides targeted delivery compositions and methods for using the compositions for treating and diagnosing a disease state in a subject. The disclosed compositions and methods provide a number of beneficial features over currently existing approaches. For example, the targeted delivery compositions include linking groups that can be synthesized to have a discrete number of monomers, which can be tailored to, e.g., provide a specific length and/or chemical property. Furthermore, the linking groups are fully customizable and can be prepared to include only one type of monomer or multiple types of monomers in any order. The linking groups can also be synthesized on a solid phase support, which allows for simple, automated syntheses. The targeted delivery compositions can be used to treat diseases more effectively by utilizing lower doses of agents that can be toxic to patients if administered with normal dosage amounts.

Entry into this solid tumor microenvironment can be achieved by allowing $MMP^i$ targeted liposomes access through systemic blood supply. As a significant percentage of tumor blood vessels are deficiently formed and 'leaky' and a $MMP^i$ targeted liposome now has contact with tumor stroma MMP enzyme and can partition toward the enzyme gradient. This and the EPR effect will effectively deliver the nanoparticle liposomes to the tumor stroma. Once in the stroma the $MMP^i$ targeted liposome can contact membrane bound MMP enzyme and be internalized by endocytosis and deliver liposomal encapsulated drug to the cell. Thus, a suitably anchored and linked MMP enzyme inhibitor ($MMP^i$) molecule can bind the tumor stroma and, if properly designed, be internalized into cells expressing membrane bound MMP enzymes, thus delivering nanoparticle/cytotoxic drug into the tumor or tumor stromal cell.

III. Targeted Delivery Compositions

A. Targeted Delivery Compositions Including a Nanocarrier

In one aspect, the targeted delivery compositions of the present invention can include a targeted delivery composition, comprising: (a) a nanocarrier including a therapeutic or diagnostic agent or a combination thereof; and (b) a conjugate having the formula: A-(LPEG)-$MMP^i$. For such conjugates, A is an attachment component for attaching the conjugate to the nanocarrier and $MMP^i$ in an inhibitor of MMP. (LPEG) is selected from: i) a linking group having from one to three polyethylene glycol components; ii) a linking group having the formula $[(EG)(P)]_m$; and iii) a linking group having the formula —$Z^1$—$Z^2$—$Z^3$—. For linking groups having the formula $[(EG)(P)]_m$, EG represents an ethylene glycol component (e.g., ethylene glycol, triethylene glycol, tetraethylene glycol, hexaethylene glycol, and the like) and P represents a phosphoryl or thiophosphoryl group, and the subscript m is an integer of from 1 to 15. For linking groups having the formula —$Z^1$—$Z^2$—$Z^3$—, $Z^1$ and $Z^3$ are independently selected from the group consisting of a PEG component having a defined length and $W^n$, wherein W is an amino acid and the subscript n is an integer from 0 to 3; and $Z^2$ is selected from the group consisting of a PEG component having a defined length and a coupling group selected from an amide, thioamide, ester, carbamate or urea for connecting $Z^1$ and $Z^3$.

Nanocarriers

A wide variety of nanocarriers can be used in constructing the targeted delivery compositions. As will be appreciated by one of ordinary skill in the art, the characteristics of the nanocarriers, e.g., size, can depend on the type and/or use of the nanocarrier as well as other factors generally well known in the art. Suitable particles can be spheres, spheroids, flat, plate-shaped, tubes, cubes, cuboids, ovals, ellipses, cylinders, cones, or pyramids. Suitable nanocarriers can range in size of greatest dimension (e.g., diameter) from about 1 nm to about 1000 nm, from about 10 nm to about 200 nm, and from about 50 nm to about 150 nm.

Suitable nanocarriers can be made of a variety of materials generally known in the art. In some embodiments, nanocarriers can include one substance or any combination of a variety of substances, including lipids, polymers, silica, or metallic materials, such as gold, iron oxide, and the like. Examples of nanocarriers can include but are not limited to a liposome, a micelle, a lipoprotein, a lipid-coated bubble, a block copolymer micelle, a polymersome, a niosome, an iron oxide particle, a gold particle, a silica particle, a dendrimer, or a quantum dot.

In some embodiments, the nanocarriers are liposomes composed partially or wholly of saturated or unsaturated lipids. Suitable lipids can include but are not limited to fats, waxes, sterols, cholesterol, fat-soluble vitamins, monoglycerides, diglycerides, phospholipids, sphingolipids, glycolipids, derivatized lipids, and the like. In some embodiments, suitable lipids can include amphipathic, neutral, non-cationic, anionic, cationic, or hydrophobic lipids. In certain embodiments, lipids can include those typically present in cellular membranes, such as phospholipids and/or sphingolipids. Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI). Suitable sphingolipids include but are not limited to sphingosine, ceramide, sphingomyelin, cerebrosides, sulfatides, gangliosides, and phytosphingosine. Other suitable lipids can include lipid extracts, such as egg PC, heart extract, brain extract, liver extract, and soy PC. In some embodiments, soy PC can include Hydro Soy PC(HSPC). Cationic lipids include but are not limited to N,N-dioleoyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA). Non-cationic lipids include but are not limited to dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. In certain embodiments, the lipids can include derivatized lipids, such as PEGlyated lipids. Derivatized lipids can include, for example, DSPE-PEG2000, cholesterol-PEG2000, DSPE-polyglycerol, or other derivatives generally well known in the art.

Any combination of lipids can be used to construct a nanocarrier such as a liposome. In certain embodiments, the lipid composition of a targeted delivery composition, such as a liposome, can be tailored to affect characteristics of the liposomes, such as leakage rates, stability, particle size, zeta potential, protein binding, in vivo circulation, and/or accumulation in tissue, such as a tumor, liver, spleen or the like. For example, DSPC and/or cholesterol can be used to decrease leakage from the liposomes. Negatively or positively lipids, such as DSPG and/or DOTAP, can be included to affect the surface charge of a liposome. In some embodiments, the liposomes can include about ten or fewer types of lipids, or about five or fewer types of lipids, or about three or fewer types of lipids. The molar percentage (mol %) of a specific type of lipid present typically ranges from about 0% to about 10%, from about 10% to about 30%, from about 30% to about 50%, from about 50% to about 70%, from about 70% to about 90%, or from about 90% to 100% of the total lipid present in a nanocarrier such as a liposome. The lipids described herein can be included in a liposome, or the lipids can be used to coat a nanocarrier of the invention, such as a polymer nanocarrier. Coatings can be partially or wholly surrounding a nanocarrier and can include monolayers and/or bilayers. In one embodiment, liposomes can be composed of about 50.6 mol % HSPC, about 44.3 mol % cholesterol, and about 5.1 mol % DSPE-PEG2000.

In other embodiments, a portion or all of a nanocarrier can include a polymer, such as a block copolymer or other polymers known in the art for making nanocarriers. In some embodiments, the polymers can be biodegradable and/or biocompatible. Suitable polymers can include but are not limited to polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, and combinations thereof. In some embodiments, exemplary particles can include shell cross-linked knedels, which are further described in the following references: Becker et al., U.S. application Ser. No. 11/250,830; Thurmond, K. B. et al., *J. Am. Chem. Soc.*, 119 (28) 6656-6665 (1997)); Wooley, K. L., *Chem. Eur.* 0.1, 3 (9): 1397-1399 (1997); Wooley, K. L., *J. Poly. Sci.: Part A: Polymer Chem.*, 38: 1397-1407 (2000). In other embodiments, suitable particles can include poly(lactic co-glycolic acid) (PLGA) (Fu, K. et al., *Pharm Res.*, 27:100-106 (2000).

Conjugates for Attaching to a Nanocarrier

In certain embodiments, the targeted delivery compositions including a nanocarrier also can include a conjugate having the formula: A-(LPEG)-MMP$^i$, wherein the attachment component A can be used to attach the conjugate to a nanocarrier. The attachment component can attach to any location on the nanocarrier, such as on the surface of the nanocarrier. The attachment component can attach to the nanocarrier through a variety of ways, including covalent and/or non-covalent attachment. As described further below, the conjugate also includes a linking group (LPEG) and an MMP$^i$ targeting agent.

In certain embodiments, the attachment component A can include a functional group that can be used to covalently attach the attachment component to a reactive group present on the nanocarrier. The functional group can be located anywhere on the attachment component, such as the terminal position of the attachment component. A wide variety of functional groups are generally known in the art and can be reacted under several classes of reactions, such as but not limited to nucleophilic substitutions (e.g., reactions of amines and alcohols with acyl halides or active esters), electrophilic substitutions (e.g., enamine reactions) and additions to carbon-carbon and carbon-heteroatom multiple bonds (e.g., Michael reaction or Diels-Alder addition). These and other useful reactions are discussed in, for example, March, *Advanced Organic Chemistry*, 3rd Ed., John Wiley & Sons, New York, 1985; and Hermanson, *Bioconjugate Techniques*, Academic Press, San Diego, 1996. Suitable functional groups can include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido groups; (e) aldehyde or ketone groups for derivatization via formation of carbonyl derivatives such as, for example, imines, hydrazones, semicarbazones or oximes, or via such reactions as Grignard addition or alkyllithium addition; (f) sulfonyl halide groups for subsequent reaction with amines, for example, to form sulfonamides; (g) thiol groups, which can be converted to disulfides or reacted with acyl halides or Michael acceptors; (h) amine or sulfhydryl groups, which can be, for example, acylated, alkylated or oxidized; (i) alkenes, which can undergo, for example, cycloadditions, acylation, Michael addition, etc.; and (j) epoxides, which can react with, for example, amines and hydroxyl compounds. In some embodiments, click chemistry-based platforms can be used to attach the attachment component to a nanocarrier (Kolb, H. C. et al. M. G. Finn and K. B. Sharpless, *Angew. Chem. Int'l. Ed.* 40 (11): 2004-2021 (2001)). In some embodiments, the attachment component can include one functional group or a plurality of functional groups that result in a plurality of covalent bonds with the nanocarrier.

Table 1 provides an additional non-limiting, representative list of functional groups that can be used in the present invention.

TABLE 1

Exemplary Functional Group Pairs for Conjugation Chemistry

| Functional Groups: | Reacts with: |
| --- | --- |
| Ketone and aldehyde groups | Amino, hydrazido and aminooxy |
| Imide | Amino, hydrazido and aminooxy |
| Cyano | Hydroxy |
| Alkylating agents (such as haloalkyl groups and maleimido derivatives) | Thiol, amino, hydrazido, aminooxy |
| Carboxyl groups (including activated carboxyl groups) | Amino, hydroxyl, hydrazido, aminooxy |
| Activated sulfonyl groups (such as sulfonyl chlorides) | Amino, hydroxyl, hydrazido, aminooxy |
| Sulfhydryl | Sulfhydryl |
| His-tag (such as 6-His tagged peptide or protein) | Nickel nitriloacetic acid |

In other embodiments, an attachment component can be attached to a nanocarrier by non-covalent interactions that can include but are not limited to affinity interactions, metal coordination, physical adsorption, hydrophobic interactions, van der Waals interactions, hydrogen bonding interactions, magnetic interactions, electrostatic interactions, dipole-dipole interactions, antibody-binding interactions, hybridization interactions between complementary DNA, and the like. In some embodiments, an attachment component can be present in a lipid bilayer portion of a nanocarrier such as a liposome. For example, an attachment component can be a lipid that interacts partially or wholly with the hydrophobic and/or hydrophilic regions of the lipid bilayer. In some embodiments, the attachment component can include one group that allows non-covalent interaction with the nanocarrier, but a plurality of groups is also contemplated. For example, a plurality of ionic charges can be used to produce sufficient non-covalent interaction between the attachment component and the nanocarrier. In alternative embodiments, the attachment component can include a plurality of lipids such that the plurality of lipids interacts with a bilayer membrane of a liposome or bilayer or monolayer coated on a nanocarrier. In certain embodiments, surrounding solution conditions can be modified to disrupt non-covalent interactions thereby detaching the attachment component from the nanocarrier.

Linking Groups

Linking groups designated (LPEG) are another feature of the targeted delivery conjugates used in the compositions provided herein. One of ordinary skill in the art can appreciate that a variety of linking groups are known in the art and can be found, for example, in the following reference: Hermanson, G. T., *Bioconjugate Techniques*, 2$^{nd}$ Ed., Academic Press, Inc. (2008). Linking groups of the present invention can be used to provide additional properties to the composition, such as providing spacing between different portions of a conjugate, e.g., A and $MMP^i$. This spacing can be used, for example, to overcome steric hindrance issues caused by the nanocarrier, e.g., when a targeting agent binds to a target. In some embodiments, linking groups can be used to change the physical properties of the targeted delivery composition.

In one group of embodiments, the linking group (LPEG) has the formula:

$$-Z^1-Z^2-Z^3-.$$

In some embodiments, $Z^1$ and $Z^3$ are independently selected from the group consisting of a PEG component having a defined length and $W_n$, wherein W is an amino acid and the subscript n is an integer from 0 to 3; and $Z^2$ is selected from the group consisting of a PEG component having a defined length and a coupling group selected from an amide, thioamide, ester, carbamate or urea for connecting $Z^1$ and $Z^3$. In some embodiments, (LPEG) is $-Z^1-Z^2-Z^3-$. In some embodiments, $Z^1$ is 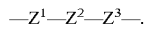; $Z^2$ is selected from an amide, thioamide, ester, carbamate urea, or combination thereof; and $Z^3$ is a PEG component having a defined length. In some embodiments, the subscript n is 1. In some embodiments, the subscript n is 2. In some embodiments, the subscript n is 3. In some embodiments, the subscript n is 0. In those embodiments where the subscript n is other than 0, the amino acid W can be an α-amino acid. The linking groups can contain any suitable α-amino acid. Examples of suitable α-amino acids include, but are not limited to, alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine. In some embodiments, the α-amino acid is selected from the group consisting of aspartic acid, glutamic acid, lysine, arginine, and glycine. In some embodiments, the α-amino acid is selected from the group consisting of glutamic acid and lysine. In some embodiments, the α-amino acid is lysine.

In some embodiments, each of $Z^1$ and $Z^3$ are a PEG component having a defined length, and $Z^2$ is a coupling group (e.g., an amide, thioamide, ester, carbamate, urea or combination linkage group) for connecting the two PEG components. One of skill in the art will appreciate that the coupling group ($Z^2$) will often be an alkylene group having functional groups on each end which can be the same or different to facilitate assembly of $-Z^1-Z^2-Z^3-$. For example, in one group of embodiments, $Z^1$ is a PEG component attached to an attachment component (A, preferably a lipid such as a phospholipid or cardioleptin molecule). Similarly, $Z^3$ is a PEG component that is attached to $MMP^i$. A number of PEG components having known lengths and the requisite functional groups for use in linkage assemblies are commercially available or can be prepared by known methods. For example, a PEG component having the formula: $HO_2C-CH_2CH_2-(OCH_2CH_2)_{24}NH\text{-BOC}$ is readily available and has functional groups that can be selectively reacted to prepare a suitable linkage assembly. In one group of embodiments, $Z^1$ is a PEG 3400 or PEG 5000 component (77 or 140 polyethylene glycol units, respectively). In other embodiments, $Z^3$ is a PEG 1000 component (24 polyethylene glycol units). In certain selected embodiments, (LPEG) has the formula:

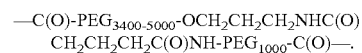

In some embodiments, (LPEG) has the formula:

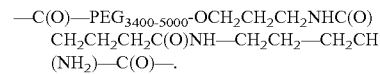

In one group of embodiments, the targeted delivery compositions can include a linking group (LPEG) having the formula: $[(EG)(P)]_m$, wherein each EG is an ethylene glycol group independently selected from triethylene glycol, tetraethylene glycol, pentaethylene glycol, hexaethylene glycol, heptaethylene glycol, and octaethylene glycol; and P is independently selected from a group consisting of phosphate and thiophosphate. In some embodiments, m can be equal to a number sufficient to make the linking group longer than a poly(ethylene glycol) moiety extending from a nanocarrier. In some embodiments, m can be greater than 1. In other embodiments, m can be an integer from 1 to 10, 1 to 20, 1 to 30, or 1 to 40. In yet other embodiments, m can be an integer from 2 to 12, 3 to 12, 4 to 12, 5 to 12, 6 to 12, 7 to 12, 8 to 12, 9 to 12, 10 to 12 and 11 to 12. In yet other embodiments, m can range from 4 to 20, 6 to 20, 8 to 20, 10 to 20, 12 to 20, 14 to 20, 16 to 20, and 18 to 20. In one embodiment, m can be 8. In yet other embodiments, m can be 4, 5, 6, 7, 8, 9, 10, 11 or 12. With respect to EG and P, any combination of both can be used in the linking group. For example, the linking group can be composed of one type of ethylene glycol, such as hexaethylene glycol with only phosphate (HEGp). In other embodiments, different ethylene glycols can be used and combined with any combination of phosphate or thiophosphate. In an exemplary embodiment, the linking group can be tetraethylene glycol-phosphate-hexaethylene glycol-thiophosphate-hexaethylene glycol-phosphate-triethylene glycol-phosphate. One of ordinary skill in the art will appreciate the vast number of combinations available for the linking groups of the present invention.

Illustrated below are a few variations of the described linking groups:

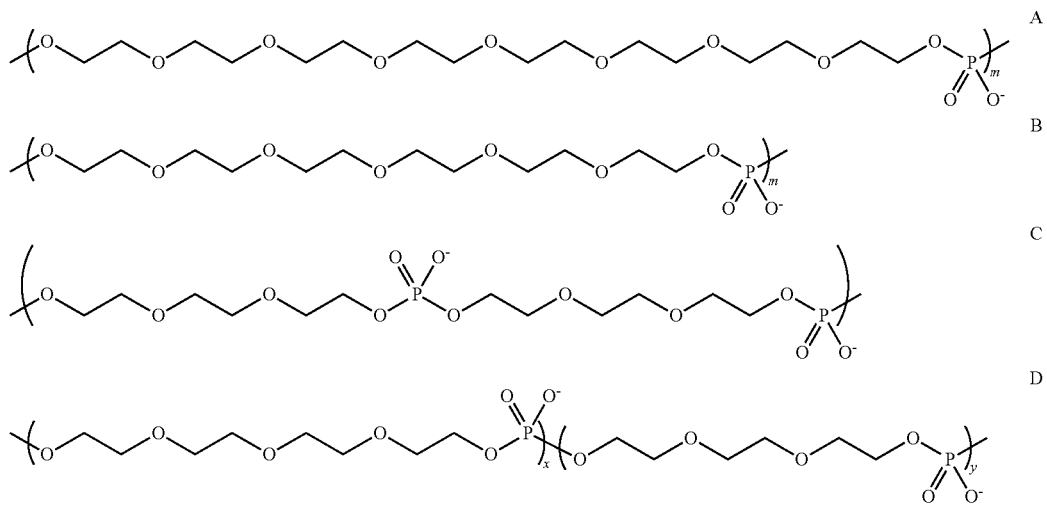

Linking group A shows an octaethylene glycol phosphate. In A, m can be, e.g., between 1 to 20. A can, also, optionally be part of another linking group, or A can be attached to another linking group. Similarly, linking group B shows a hexaethylene glycol phosphate (also described herein as HEGp). B can include a number of repeat units, e.g., m can be between 1 to 20, or preferably about 8. As shown in linking group C, m can equal a specific integer, e.g., m=2, as depicted by an exemplary dimer of triethylene glycol phosphate. Alternatively, linking groups can, e.g., be described using additional subscripts, x and y, such that x+y=m. Linking group D, for example, shows a tetraethylene glycol phosphate linked to a triethylene glycol phosphate. In certain embodiments, the ethylene glycol portions (EG) within the subscripted brackets of x and y can be independently selected from a group consisting of triethylene glycol, tetraethylene glycol, pentaethylene glycol, hexaethylene glycol, heptaethylene glycol, and octaethylene glycol.

Therapeutic Agents

The nanocarriers used in the targeted therapeutic or diagnostic delivery compositions of the present invention include a therapeutic agent, diagnostic agent, or a combination thereof. The therapeutic agent and/or diagnostic agent can be present anywhere in, on, or around the nanocarrier. In some embodiments, the therapeutic agent and/or diagnostic agent can be embedded in, encapsulated in, or tethered to the nanocarrier. In certain embodiments, the nanocarrier is a liposome and the diagnostic and/or therapeutic agent is encapsulated in the liposome.

A therapeutic agent used in the present invention can include any agent directed to treat a condition in a subject. In general, any therapeutic agent known in the art can be used, including without limitation agents listed in the United States Pharmacopeia (U.S.P.), *Goodman and Gilman's The Pharmacological Basis of Therapeutics*, 10th Ed., McGraw Hill, 2001; Katzung, Ed., *Basic and Clinical Pharmacology*, McGraw-Hill/Appleton & Lange, 8th ed., Sep. 21, 2000; *Physician's Desk Reference* (Thomson Publishing; and/or *The Merck Manual of Diagnosis and Therapy*, 18th ed., 2006, Beers and Berkow, Eds., Merck Publishing Group; or, in the case of animals, *The Merck Veterinary Manual*, 9th ed., Kahn Ed., Merck Publishing Group, 2005; all of which are incorporated herein by reference.

Therapeutic agents can be selected depending on the type of disease desired to be treated. For example, certain types of cancers or tumors, such as carcinoma, sarcoma, leukemia, lymphoma, myeloma, and central nervous system cancers as well as solid tumors and mixed tumors, can involve administration of the same or possibly different therapeutic agents. In certain embodiments, a therapeutic agent can be delivered to treat or affect a cancerous condition in a subject and can include chemotherapeutic agents, such as alkylating agents, antimetabolites, anthracyclines, alkaloids, topoisomerase inhibitors, and other anticancer agents. In some embodiments, the agents can include antisense agents, microRNA, siRNA and/or shRNA agents.

In some embodiments, a therapeutic agent can include an anticancer agent or cytotoxic agent including but not limited to avastin, doxorubicin, cisplatin, oxaliplatin, carboplatin, 5-fluorouracil, gemcitibine or taxanes, such as paclitaxel and docetaxel. Additional anti-cancer agents can include but are not limited to 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, cam 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflomithine, eflomithine hydrochloride, elemene, elsamitrucin, emitefur, enloplatin, enpromate, epipropidine, epirubicin, epirubicin hydrochloride, episteride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride or suitable prodrugs of the aforementioned drugs.

In some embodiments, the therapeutic agents can be part of cocktail of agents that includes administering two or more therapeutic agents. For example, a liposome having both cisplatin and oxaliplatin can be administered. In addition, the therapeutic agents can be delivered before, after, or with immune stimulatory adjuvants, such as aluminum gel or salt adjuvants (e.g., alumimum phosphate or aluminum hydroxide), calcium phosphate, endotoxins, toll-like receptor adjuvants and the like.

Therapeutic agents of the present invention can also include radionuclides for use in therapeutic applications. For example, emitters of Auger electrons, such as $^{111}$In, can be combined with a chelate, such as diethylenetriaminepentaacetic acid (DTPA) or 1,4,7,10-tetraazacyclododecane-1,4,7,10-tetraacetic acid (DOTA), and included in a targeted delivery composition, such as a liposome, to be used for treatment. Other suitable radionuclide and/or radionuclide-chelate combinations can include but are not limited to beta radionuclides ($^{177}$Lu, $^{153}$Sm, $^{88/90}$Y) with DOTA, $^{64}$Cu-TETA, $^{188/186}$Re(CO)$_3$-IDA; $^{188/186}$Re(CO)triamines (cyclic or linear), $^{188/186}$Re(CO)$_3$-Enpy2, and $^{188/186}$Re(CO)$_3$-DTPA.

As described above, the therapeutic agents used in the present invention can be associated with the nanocarrier in a variety of ways, such as being embedded in, encapsulated in, or tethered to the nanocarrier. Loading of the therapeutic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006). In a group of embodiments, one or more therapeutic agents can be loaded into liposomes. Loading of liposomes can be carried out, for example, in an active or passive manner. For example, a therapeutic agent can be included during the self-assembly process of the liposomes in a solution, such that the therapeutic agent is encapsulated within the liposome. In certain embodiments, the therapeutic agent may also be embedded in the liposome bilayer or within multiple layers of multilamellar liposome. In alternative embodiments, the therapeutic agent can be actively loaded into liposomes. For example, the liposomes can be exposed to conditions, such as electroporation, in which the bilayer membrane is made permeable to a solution containing therapeutic agent thereby allowing for the therapeutic agent to enter into the internal volume of the liposomes.

Diagnostic Agents

A diagnostic agent used in the present invention can include any diagnostic agent known in the art, as provided, for example in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl)methyl] benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra (methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope can be incorporated into some of the diagnostic agents described herein and can include radionuclides that emit gamma rays, positrons, beta and alpha particles, and X-rays. Suitable radionuclides include but are not limited to $^{225}$AC, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPY2, $^{62/64/67}$Cu-TETA, $^{99m}$Tc(CO)$_3$-IDA, and $^{99m}$Tc(CO)$_3$-triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the liposomes can be radiolabeled, for example, by incorporation of lipids attached to chelates, such as DTPA-lipid, as provided in the following references: Phillips et al., *Wiley Interdisciplinary Reviews Nanomedicine and Nanobiotechnology*, 1(1): 69-83 (2008); Torchilin, V. P. & Weissig, V., Eds. *Liposomes* 2nd Ed.: Oxford Univ. Press (2003); Elbayoumi, T. A. & Torchilin, V. P., *Eur. J. Nucl. Med. Mol. Imaging.* 33:1196-1205 (2006); Mougin-Degraef, M. et al., *Int'l J. Pharmaceutics* 344:110-117 (2007).

In other embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In some embodiments, the non-ionizing radiation employed in the process of the present invention can range in wavelength from about 350 nm to about 1200 nm. In one exemplary embodiment, the fluorescent agent can be excited by light having a wavelength in the blue range of the visible portion of the electromagnetic spectrum (from about 430 nm to about 500 nm) and emits at a wavelength in the green range of the visible portion of the electromagnetic spectrum (from about 520 nm to about 565 nm). For example, fluorescein dyes can be excited with light with a wavelength of about 488 nm and have an emission wavelength of about 520 nm. As another example, 3,6-diaminopyrazine-2,5-dicarboxylic acid can be excited with light having a wavelength of about 470 nm and fluoresces at a wavelength of about 532 nm. In another embodiment, the excitation and emission wavelengths of the optical agent may fall in the near-infrared range of the electromagnetic spectrum. For example, indocyanine dyes, such as indocyanine green, can be excited with light with a wavelength of about 780 nm and have an emission wavelength of about 830 nm.

In yet other embodiments, the diagnostic agents can include but are not limited to magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., Diagnostic Imaging, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to Gadopentetic acid, Gadoteric acid, Gadodiamide, Gadolinium, Gadoteridol, Mangafodipir, Gadoversetamide, Ferric ammonium citrate, Gadobenic acid, Gadobutrol, or Gadoxetic acid. Superparamagnetic agents can include but are not limited to superparamagnetic iron oxide and Ferristene. In certain embodiments, the diagnostic agents can include x-ray contrast agents as provided, for example, in the following references: H. S Thomsen, R. N. Muller and R. F. Mattrey, Eds., Trends in Contrast Media, (Berlin: Springer-Verlag, 1999); P. Dawson, D. Cosgrove and R. Grainger, Eds., Textbook of Contrast Media (ISIS Medical Media 1999); Torchilin, V. P., Curr. Pharm. Biotech. 1:183-215 (2000); Bogdanov, A. A. et al., Adv. Drug Del. Rev. 37:279-293 (1999); Sachse, A. et al., Investigative Radiology 32(1):44-50 (1997). Examples of x-ray contrast agents include, without limitation, iopamidol, iomeprol, iohexyl, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexyl, iopentol, ioversol, iobitridol, iodixanol, iotrolan and iosimenol.

Similar to therapeutic agents described above, the diagnostic agents can be associated with the nanocarrier in a variety of ways, including for example being embedded in, encapsulated in, or tethered to the nanocarrier. Similarly, loading of the diagnostic agents can be carried out through a variety of ways known in the art, as disclosed for example in the following references: de Villiers, M. M. et al., Eds., Nanotechnology in Drug Delivery, Springer (2009); Gregoriadis, G., Ed., Liposome Technology: Entrapment of drugs and other materials into liposomes, CRC Press (2006).

Targeting Agents

The targeted delivery compositions of the present invention also include MMP$^i$, a targeting agent. Generally, MMP$^i$ refers to any matrix metalloproteinase inhibitor. In certain embodiments, MMP$^i$ is an inhibitor having the formula:

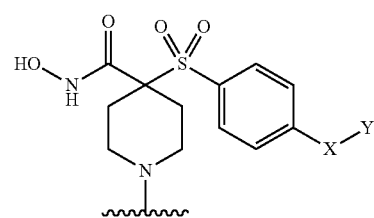

wherein

X is a member selected from the group consisting of O and S;

Y is a member selected from the group consisting of pyridyl and phenyl, wherein said phenyl is optionally substituted with OH, OCH$_3$, OCF$_3$ and CH$_3$; and the wavy line indicates the point of attachment to (LPEG).

In certain specific embodiments, MMP$^i$ is selected from:

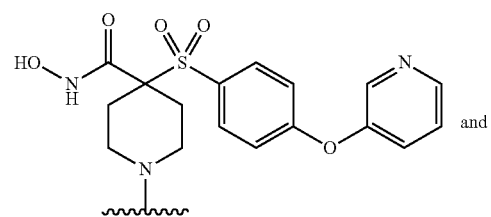

and

-continued

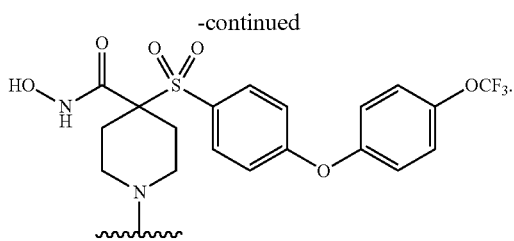

In certain specific embodiments, MMP$^i$ is selected from:

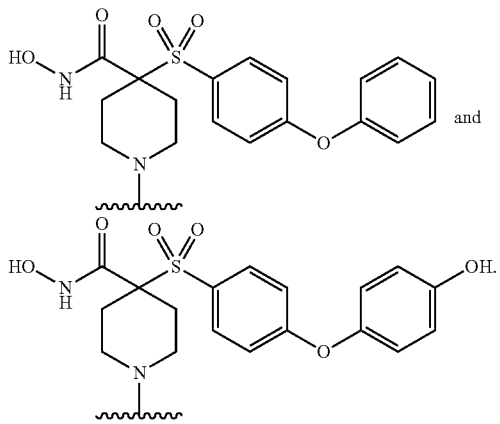

B. Individual Components of the Targeted Delivery Compositions Including a Nanocarrier In another aspect, the present invention provides individual components of the targeted delivery compositions disclosed herein. In particular, the present invention includes a conjugate having the formula: A-(LPEG)-MMP$^i$; wherein, A is an attachment component; (LPEG) is a linking group as described above; and, MMP$^i$ is a MMP inhibitor.

It will be appreciated by one of ordinary skill in the art that components of the targeted delivery compositions similarly include each of the specific embodiments described above.

IV. Methods of Preparing Targeted Delivery Compositions and Components

A. Targeted Delivery Compositions Including a Nanocarrier

The targeted delivery compositions of the present invention can be produced in a variety of ways. In one aspect, targeted delivery compositions of the present invention can be prepared by attaching a nanocarrier to a conjugate having the formula: A-(LPEG)-MMP$^i$; wherein, A is an attachment component for attaching said conjugate to said nanocarrier; (LPEG) is a linking group; and, MMP$^i$ is a MMP inhibitor. The nanocarrier can be contacted with the conjugate either as a loaded nanocarrier (e.g., having incorporated a therapeutic or diagnostic agent) or an unloaded nanocarrier.

Nanocarriers

Nanocarriers can be produced by a variety of ways generally known in the art and methods of making such nanocarriers can depend on the particular nanocarrier desired. Any measuring technique available in the art can be used to determine properties of the targeted delivery compositions and nanocarriers. For example, techniques such as dynamic light scattering, x-ray photoelectron microscopy, powder x-ray diffraction, scanning electron microscopy (SEM), transmission electron microscopy (TEM), and atomic force microscopy (AFM) can be used to determine average size and dispersity of the nanocarriers and/or targeted delivery compositions.

Liposomes used in the targeted delivery compositions of the present invention can be made using a variety of techniques generally well known in the art. (See, e.g., Williams, A. P., Liposomes: A Practical Approach, 2$^{nd}$ Edition, Oxford Univ. Press (2003); Lasic, D. D., Liposomes in Gene Delivery, CRC Press LLC (1997)). For example, liposomes can be produced by but are not limited to techniques such as extrusion, agitation, sonication, reverse phase evaporation, self-assembly in aqueous solution, electrode-based formation techniques, microfluidic directed formation techniques, and the like. In certain embodiments, methods can be used to produce liposomes that are multilamellar and/or unilamellar, which can include large unilamellar vesicles (LUV) and/or small unilamellar vesicles (SUV). Similar to self-assembly of liposomes in solution, micelles can be produced using techniques generally well known in the art, such that amphiphilic molecules will form micelles when dissolved in solution conditions sufficient to form micelles. Lipid-coated bubbles and lipoproteins can also be constructed using methods known in the art (See, e.g., Farook, U., J. R. Soc. Interface, 6(32): 271-277 (2009); Lacko et al., Lipoprotein Nanocarriers as Delivery Vehicles for Anti-Cancer Agents in Nanotechnology for Cancer Therapy, CRC Press (2007)).

Methods of making polymeric nanocarriers that can be used in the present invention are generally well known in the art (See, e.g., Sigmund, W. et al., Eds., Particulate Systems in Nano- and Biotechnologies, CRC Press LLC (2009); Karnik et al., Nano Lett., 8(9): 2906-2912 (2008)). For example, block copolymers can be made using synthetic methods known in the art such that the block copolymers can self-assemble in a solution to form polymersomes and/or block copolymer micelles. Niosomes are known in the art and can be made using a variety of techniques and compositions (Baillie A. J. et al., J. Pharm. Pharmacol., 38:502-505 (1988)). Magnetic and/or metallic particles can be constructed using any method known in the art, such as co-precipitation, thermal decomposition, and microemulsion. (See also Nagarajan, R. & Hatton, T. A., Eds., Nanocarriers Synthesis, Stabilization, Passivation, and Functionalization, Oxford Univ. Press (2008)). Gold particles and their derivatives can be made using a variety of techniques generally known in the art, such as the Turkevich method, Brust method, Perraut Method or sonolysis (See also, Grzelczak et al., Chem. Soc. Rev., 37: 1783-1791 (2008)). In some embodiments, the attachment component can be attached through sulfur-gold tethering chemistry. Quantum dots or semiconductor nanocrystals can be synthesized using any method known in the art, such as colloidal synthesis techniques.

Conjugates for Attaching to a Nanocarrier

The conjugates having the formula A-[(EG)(P)]$_m$-MMP$^i$, as described herein, can be manufactured using a variety of techniques. In some embodiments, the entire conjugate can be synthesized in oligonucleotide synthesizers well known in the art. In certain embodiments, incorporation of [(EG)(P)]$_m$, such as (HEGp)$_m$, can be performed using modified synthesis cycles for more effective incorporation. In particular, increased amidite equivalents and extended wash cycles can incorporate multiple [(EG)(P)] units as linking groups in the conjugates of the present invention. In certain embodiments, an attachment component, such as cholesterol or a cholesterol derivative (e.g., cholesterol-tetraethylene glycol) can then be added using standard or modified synthesis cycles, which can include doubling the coupling recycle step to insure effective incorporation. In certain embodiments, the conjugates can be synthesized using solid phase approaches, such as silica-based or polystyrene-based supports.

In other embodiments, the $[(EG)(P)]_m$ linking group can be attached to an attachment component, such as a cholesterol derivative (cholesterol-tetraethylene glycol), using conventional chemistry known in the art. The $[(EG)(P)]_m$ linking group can be synthesized using the methods described above. Next, the linking group and the attachment component can be mixed and reacted under conditions sufficient to form a portion of the conjugate, $A-[(EG)(P)]_m$. Subsequently, a targeting agent, $MMP^i$, can be attached to the other end of the $[(EG)(P)]_m$ linking group. Alternatively, the targeting agent can be attached to the $[(EG)(P)]_m$ linking group first, followed by the attachment component. As will be appreciated by one of ordinary skill in the art, targeting agents of the present invention can be attached to the $[(EG)(P)]_m$ linking group by a variety of ways that can depend on the characteristics of the specific $MMP^i$ component.

V. Methods of Administering Targeted Delivery Compositions

As described herein, the targeted delivery compositions and methods of the present invention can be used for treating and/or diagnosing any disease, disorder, and/or condition associated with a subject. In one embodiment, the methods of the present invention include a method for treating or diagnosing a cancerous condition in a subject, comprising administering to the subject a targeted delivery composition of the present invention that includes a nanocarrier, wherein the therapeutic or diagnostic agent is sufficient to treat or diagnose the condition. In certain embodiments, the cancerous condition can include cancers that sufficiently express (e.g., on the cell surface or in the vasculature) a receptor that is being targeted by a targeting agent of a targeted delivery composition of the present invention.

In another embodiment, the methods of the present invention include a method of determining the suitability of a subject for a targeted therapeutic treatment, comprising administering to the subject a targeted delivery composition that includes a nanocarrier, wherein the nanocarrier comprises a diagnostic agent, and imaging the subject to detect the diagnostic agent.

Administration

In some embodiments, the present invention can include a targeted delivery composition and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized targeted delivery compositions.

The targeted delivery composition of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which includes an effective amount of a packaged targeted delivery composition with a suppository base. Suitable suppository bases include natural or synthetic triglycerides or paraffin hydrocarbons. In addition, it is also possible to use gelatin rectal capsules which contain a combination of the targeted delivery composition of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of targeted delivery compositions can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a targeted delivery composition. The unit dosage form can be a packaged preparation, the package containing discrete quantities of preparation. The composition can, if desired, also contain other compatible therapeutic agents.

In therapeutic use for the treatment of cancer, the targeted delivery compositions including a therapeutic and/or diagnostic agent utilized in the pharmaceutical compositions of the present invention can be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the targeted delivery composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted delivery composition in a particular patient. Determination of the proper dosage for a particular situation is within the skill of the practitioner. Generally, treatment is initiated with smaller dosages which are less than the optimum dose of the targeted delivery composition. Thereafter, the dosage is increased by small increments until the optimum effect under circumstances is reached. For convenience, the total daily dosage may be divided and administered in portions during the day, if desired.

In some embodiments, the targeted delivery compositions of the present invention may be used to diagnose a disease, disorder, and/or condition. In some embodiments, the targeted delivery compositions can be used to diagnose a cancerous condition in a subject, such as lung cancer, breast cancer, pancreatic cancer, prostate cancer, cervical cancer, ovarian cancer, colon cancer, liver cancer, esophageal cancer, and the like. In some embodiments, methods of diagnosing a disease state may involve the use of the targeted delivery compositions to physically detect and/or locate a tumor within the body of a subject. For example, tumors can be related to cancers that sufficiently express (e.g., on the cell surface or in the vasculature) a receptor that is being targeted by a targeting agent of a targeted delivery composition of the present invention. In some embodiments, the targeted delivery compositions can also be used to diagnose diseases other than cancer, such as proliferative diseases, cardiovascular diseases, gastrointestinal diseases, genitourinary disease, neurological diseases, musculoskeletal diseases, hematological diseases, inflammatory diseases, autoimmune diseases, rheumatoid arthritis and the like.

As disclosed herein, the targeted delivery compositions of the invention can include a diagnostic agent that has intrinsically detectable properties. In detecting the diagnostic agent in a subject, the targeted delivery compositions, or a population of particles with a portion being targeted delivery compositions, can be administered to a subject. The subject can then be imaged using a technique for imaging the diagnostic agent, such as single photon emission computed tomography (SPECT), magnetic resonance imaging (MRI), optical imaging, positron emission tomography (PET), computed tomography (CT), x-ray imaging, gamma ray imaging, and the like. Any of the imaging techniques described herein may be used in combination with other imaging techniques. In some embodiments, the incorporation of a radioisotope for imaging in a particle allows in vivo tracking of the targeted delivery compositions in a subject. For example, the biodistribution and/or elimination of the targeted delivery compositions can be measured and optionally be used to alter the treatment of patient. For example, more or less of the targeted delivery compositions may be needed to optimize treatment and/or diagnosis of the patient.

Targeted Delivery

In certain embodiments, the targeted delivery compositions of the present invention can be delivered to a subject to release a therapeutic or diagnostic agent in a targeted manner. For example, a targeted delivery composition can be delivered to a target in a subject and then a therapeutic agent embedded in, encapsulated in, or tethered to the targeted delivery composition, such as to the nanocarrier, can be delivered based on solution conditions in vicinity of the target. Solution conditions, such as pH, salt concentration, and the like, may trigger release over a short or long period of time of the therapeutic agent to the area in the vicinity of the target. Alternatively, an enzyme can cleave the therapeutic or diagnostic agent from the targeted delivery composition to initiate release. In some embodiments, the targeted delivery compositions can be delivered to the internal regions of a cell by endocytosis and possibly later degraded in an internal compartment of the cell, such as a lysosome. One of ordinary skill will appreciate that targeted delivery of a therapeutic or diagnostic agent can be carried out using a variety of methods generally known in the art.

Kits

The present invention also provides kits for administering the targeted delivery compositions to a subject for treating and/or diagnosing a disease state. Such kits typically include two or more components necessary for treating and/or diagnosing the disease state, such as a cancerous condition. Components can include targeted delivery compositions of the present invention, reagents, containers and/or equipment. In some embodiments, a container within a kit may contain a targeted delivery composition including a radiopharmaceutical that is radiolabeled before use. The kits can further include any of the reaction components or buffers necessary for administering the targeted delivery compositions. Moreover, the targeted delivery compositions can be in lyophilized form and then reconstituted prior to administration.

In certain embodiments, the kits of the present invention can include packaging assemblies that can include one or more components used for treating and/or diagnosing the disease state of a patient. For example, a packaging assembly may include a container that houses at least one of the targeted delivery compositions as described herein. A separate container may include other excipients or agents that can be mixed with the targeted delivery compositions prior to administration to a patient. In some embodiments, a physician may select and match certain components and/or packaging assemblies depending on the treatment or diagnosis needed for a particular patient.

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

VI. Examples

Abbreviations mL, milliliters; HOBT, hydroxybenzotriazole; LCMS, liquid chromatography mass spectrum; DMF, dimethylformamide; DMSO, dimethyl sulfoxide; EA, ethyl acetate; H, hexane; rt, ambient temperature; h, hour(s); TLC, thin layer chromatography; TEA, triethylamine; HRMS, high resolution mass spectrum; Boc, tert-butyloxy carbonyl.

Example 1

Synthesis of MMP-Targeting Conjugate for Preparation of Targeted Delivery Compositions Step 1: Preparation of 1-tert-butyl 4-ethyl 4-(4-(pyridin-3-yloxy)phenylsulfonyl)piperidine-1,4-dicarboxylate 1-tert-butyl 4-ethyl 4-(4-(pyridin-3-yloxy)phenylsulfonyl) piperidine-1,4-dicarboxylate was prepared according to FIG.

2. A round bottom flask (100 mL) equipped with magnetic stir bar (Teflon covered) and condenser was charged with 1.5 g p-fluoro-sulfone, 0.5 g (1.5 eq.) 3-hydroxy pyridine and 1.76 g (1.5 eq.) cesium carbonate in DMF (50 mL). The reaction was heated to 90° C. for 18 hours. LCMS after 2 hours shows desired product at 4.4 min and starting material sulfone at 4.8 minutes. Volatiles were removed and the residue partitioned between ethyl acetate and saturated aqueous sodium bicarbonate. The organic layer was washed with 10% aqueous citric acid, aqueous sodium bicarbonate, brine, and dried with anhydrous sodium sulfate. TLC (silica) shows one spot (40% ethyl acetate:hexane). Ethyl acetate was removed and the resulting amber semi solid was vacuum dried to obtain 1.72 g of product as an amber foam. $^1$H-NMR (DMSO-d6) is consistent with desired product. This intermediate was used in the next step without further purification.

Figure 3:
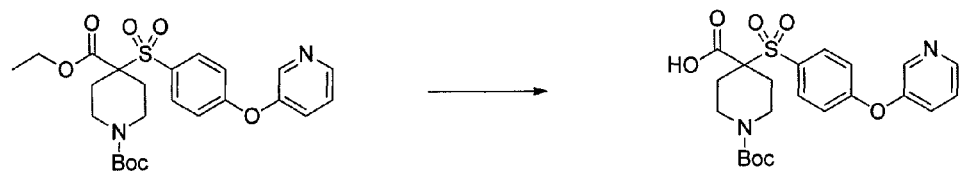
FIG. 3 shows the synthesis of 1-(tert-butoxycarbonyl)-4-(4-(pyridin-3-yloxy)phenylsulfonyl)piperidine-4-carboxylic acid.

Step 2. Preparation of 1-(tert-butoxycarbonyl)-4-(4-(pyridin-3-yloxy)phenylsulfonyl)piperidine-4-carboxylic acid 1-(tert-butoxycarbonyl)-4-(4-(pyridin-3-yloxy)phenylsulfonyl)piperidine-4-carboxylic acid was prepared according to FIG. 3. A 250-mL round bottom flask was charged with 1.7 g ethyl ester (from step 1), 0.78 g (4 eq.) potassium hydroxide in 16 mL ethanol and 4 mL water. The reaction mixture was heated to 90° C. LCMS after 1 hour shows complete reaction. The mixture was partitioned between ethyl acetate and 10% aqueous KHSO$_4$-Brine. The yellow organic phase was separated, dried, filtered and concentrated. The residue was vacuum dried overnight to produce 1.32 g off-white foam that was used without further purification.

Figure 4:
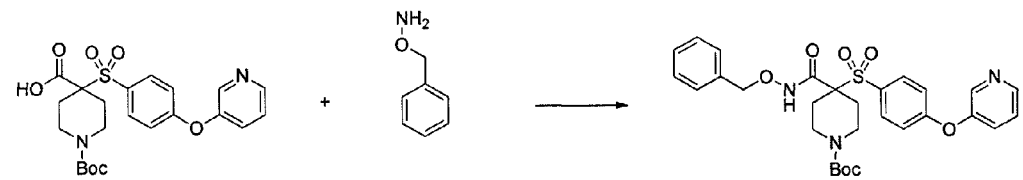
FIG. 4 shows the synthesis of tert-butyl 4-(benzyloxycarbamoyl)-4-(4-(pyridin-3-yloxy)phenylsulfonyl)piperidine-1-carboxylate.

Step 3: Preparation of tert-butyl 4-(benzyloxycarbamoyl)-4-(4-(pyridin-3-yloxy)phenylsulfonyl)piperidine-1-carboxylate tert-Butyl 4-(benzyloxycarbamoyl)-4-(4-(pyridin-3-yloxy)phenylsulfonyl)piperidine-1-carboxylate was prepared according to FIG. 4. A 100 mL round bottom flask equipped with magnetic stir bar was charged with 1.32 g acid, 0.66 g (1.2 eq.) EDC, 0.58 (1.5 eq.) HOBT, and 0.58 g (2 eq.) TEA in 15 mL CH$_2$Cl$_2$. This was stirred 10 minutes when 0.55 g (1.2 eq.) of the amine HCl salt was added. The reaction was stirred at RT. LCMS after 2 hours shows little starting material and ~1:1 mixture of product and active ester. Another 1 eq. of amine —HCl salt was added to the reaction mixture. LCMS shows a trace of acid and mostly product. The HOBt ester is not observed. The reaction was concentrated to a solid and partitioned between ethyl acetate and aqueous sodium bicarbonate. The organics were washed with 10% aqueous KHSO$_4$, brine, and dried. TLC (silica, 1:1 ethyl acetate:hexane) showed one spot (R$_f$=~0.4 and some material at the origin). The resulting ethyl acetate solution was concentrated (~10 mL) and filtered through a plug of silica gel. The silica was washed with ethyl acetate and combined organics were concentrated and vacuum dried to yield 1.29 g (80%) of an off-white foam.

Figure 5:
FIG. 5 shows the synthesis of N-(benzyloxy)-4-(4-(pyridin-3-yloxy)phenylsulfonyl)piperidine-4-carboxamide.

Step 4. Preparation of N-(benzyloxy)-4-(4-(pyridin-3-yloxy)phenylsulfonyl)piperidine-4-carboxamide N-(benzyloxy)-4-(4-(pyridin-3-yloxy)phenylsulfonyl)piperidine-4-carboxamide was prepared according to FIG. 5. A 100 mL round bottom flask was charged with 1.3 g of the Boc protected amine prepared in Step 3 and 4 N HCl-Dioxane (10 mL) and the mixture stirred for 20 minutes. LCMS after 20 minutes shows no starting material. The reaction mixture was concentrated in vacuo and vacuum dried overnight to afford N-(benzyloxy)-4-(4-(pyridin-3-yloxy)phenylsulfonyl)piperidine-4-carboxamide (1.3 g bis HCl salt) that was used without further purification.

Figure 6:
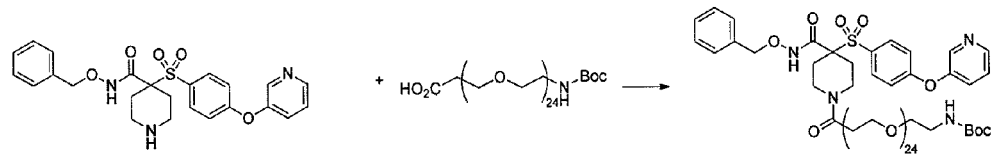
FIG. 6 shows the synthesis of a PEG 1000 piperidine amido amine derivative of N-(benzyloxy)-4-(4-(pyridin-3-yloxy)phenylsulfonyl)piperidine-4-carboxamide.

Step 5: Preparation of PEG 1000 piperidine amido amine derivative of N-(benzyloxy)-4-(4-(pyridin-3-yloxy)phenylsulfonyl)piperidine-4-carboxamide The PEG 1000 piperidine amido amine derivative of N-(benzyloxy)-4-(4-(pyridin-3-yloxy)phenylsulfonyl)piperidine-4-carboxamide was prepared according to FIG. 6. A 100 mL round bottom flask was charged with 1.16 g (1.0 eq.) PEG acid mono Boc amine, 0.25 g (1.2 eq.) EDC, 0.2 g (1.5 eq.) HOBt, and 0.09 g (1.0 eq.) TEA in 5 mL dichloromethane. 0.5 g (1.0 eq.) of the amine and 0.28 g (3.0 eq.) additional TEA were added in 7 mL dichloromethane and the reaction was stirred under argon for 10 minutes then stirred at RT overnight. The reaction was diluted with 85 mL CHCl$_3$ and washed with 15 mL deionized water, 25 mL 5% aqueous citric acid, and then a mixture of 25 mL aqueous sodium bicarbonate –25 mL brine. The organic layer stayed pale yellow and was dried (sodium sulfate, anhydrous) and concentrated in vacuo. TLC (20% MeOH—CHCl$_3$) shows R$_f$=0.4 but, more importantly, clean one spot with nothing UV visible at the origin. After concentration the product was vacuum dried to afford 1.7 g. LC-HRMS$_{(obs)}$ M+H=1695.8782 g/mol; M+NH$_4$=1712.9046 g/mol. HRMS$_{(calculated)}$ M H=1695.8775 g/mol; M+NH$_4$=1712.9040 g/mol. $^1$H-NMR (CDCl$_3$) was consistent with the desired product.

Step 6

Figure 7:
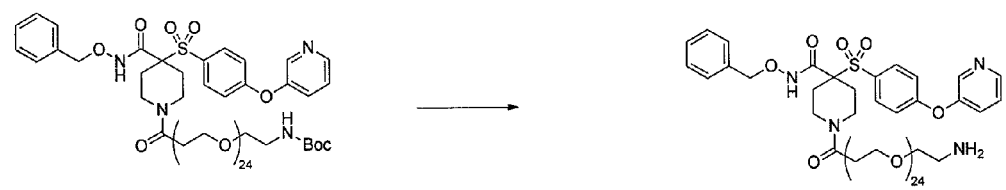
FIG. 7 shows the deprotection of the PEG 1000 piperidine amido amine derivative of N-(benzyloxy)-4-(4-(pyridin-3-yloxy)phenylsulfonyl)piperidine-4-carboxamide.

Deprotection of the PEG 1000 piperidine amido amine derivative of N-(benzyloxy)-4-(4-(pyridin-3-yloxy)phenylsulfonyl)piperidine-4-carboxamide was conducted according to FIG. 7. A 100 mL round bottom flask was charged with 1.66 g of the Boc compound in 15 mL 4 N HCl-Dioxane and tumbled for 30 minutes on a rotary evaporator. The reaction was concentrated to an oil that was subsequently vacuum dried to a clear thick yellow syrup. The de-BOC amine was obtained (1.68 g of the bis-HCl salt) and used without further purification. Material was submitted for LC-HRMS and chloride content. Cl content was determined to be 4%, consistent with 2 eq. HCl.

Step 7

Figure 8:
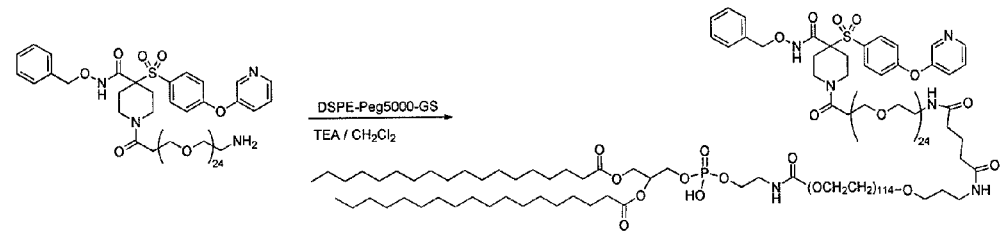
FIG. 8 shows the synthesis of a protected N-(benzyloxy)-4-(4-(pyridin-3-yloxy)phenylsulfonyl)piperidine-4-carboxamide-PEG1000-PEG5000 conjugate.

Conjugation of DSPE-PEG 5000 to the PEG 1000 piperidine amido amine derivative of N-(benzyloxy)-4-(4-(pyridin-3-yloxy)phenylsulfonyl)piperidine-4-carboxamide was conducted according to FIG. 8. A 50 mL round bottom flask was charged with 60 mg (1.0 eq.) amine prepared in Step 6 and 15 mg (4 eq.) triethylamine in 8 mL methylene chloride. NHS ester of DSPE-PEG 5000 (220 mg, 1.0 eq) was added and the reaction was stirred at RT for 2½ hours and a sample was analyzed by LCMS. The reaction was concentrated to a clear oil. This was redissolved in acetonitrile:water, frozen and lyophilized overnight to afford ~260 mg of crude white foam that was used without further purification. LC-HRMS: M/2–2H$_{(obs)}$=3780.2141 LC-HRMS M/2–2H$_{(calc)}$=3780.2244.

Step 8

Figure 9:
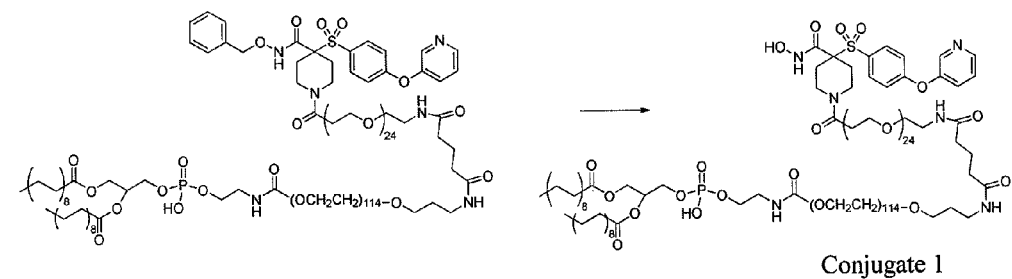
FIG. 9 shows the synthesis of an N-hydroxy-4-(4-(pyridin-3-yloxy)phenyl-sulfonyl)piperidine-4-carboxamide-PEG1000-PEG5000 conjugate (Conjugate 1).

Cleavage of the benzyl group from the N-benzyloxy-4-carboxamide moiety of the DSPE-PEG-MMPi intermediate obtained in Step 8 was conducted according to FIG. 9. A 200 mL round bottom flask equipped with magnetic stir bar containing 325 mg lyophilized benzyl ester prepared in Step 7 was charged with 15 mL methanol. Wet 10% Pd—C catalyst (75 mg, Degussa) was added and the reaction mixture was purged with argon for 10 minutes then hydrogen was slowly bubbled over the stirring solution. The reaction proceeded for 1 hour 20 minutes and then analyzed by MS. LCMS showed partial conversion to product. The reaction mixture was filtered through Celite® and washed with warm methanol (40 mL). The resulting solution was treated with fresh catalyst (75 mg) and hydrogenated for an additional 90 min. LCMS showed no starting material. The reaction mixture was purged with argon and filtered through Celite then poured through a paper funnel to remove slight cloudiness and the filtrate was concentrated in vacuo to afford a clear oil. This was dissolved in water/acetonitrile, frozen and lyophilized for 2 days. The desired DSPE-PEG-MMPi product was obtained as a dry white powder (230 mg). See FIG. 1 for LC-HRMS results.

Example 2

Procedure for Preparation of MMP$^i$ Targeted Liposomal TD-1

TD-1

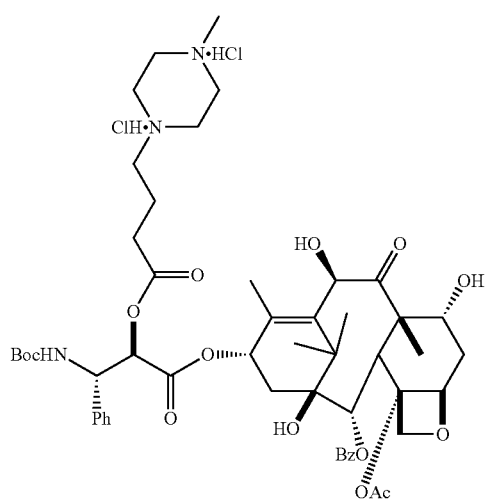

A representative procedure for the formation of MMP$^i$ targeted liposomes containing a cytotoxic pro-drug is provided in the following example.

To a 3-neck, 500 mL round-bottom flask containing a solution of 10 mM aqueous sodium acetate/300 mM sucrose at pH 5.5 (90 mL) was added TD-1 (189 mg, 0.181 mmol). Upon complete dissolution the homogeneous solution was adjusted to pH 5.50. Independently, the volume of a previously prepared solution of pre-formed liposomes (DSPC:Cholesterol (55:45)) was measured and diluted with 10 mM aqueous sodium acetate/300 mM sucrose at pH 5.5 to 100 mL. The pH of the heterogeneous solution was adjusted to pH 5.5. Both solutions were gently heated to 65° C. at which time the TD-1 solution was rapidly added to the liposome solution. The combined mixture was held at 65° C. for 15 min., then cooled to 55° C. Meanwhile, DSPE-PEG(2000) obtained from Lipoid (138 mg, 0.049 mmol) and Conjugate 1 (see previous example, 5 mg, 0.553 umol) was dissolved in solution of 10 mM acetate/300 mM sucrose at pH 5.5 (5 mL). Once the TD-1/liposome mixture reached 55° C., the pH was measured (pH 5.98), particle size (intensity and volume) was obtained (Z.Ave.=109.4 nm), and the homogeneous solution of Lipoid/Conjugate 1 target was added. The resulting mixture was heated at 55° C. for 30 min then allowed to cool to room temperature. The pH was measured (pH 5.89), particle size (intensity and volume) was obtained (Z.Ave.=117.0). This liposome solution was concentrated to 60 mL, then diafiltered against 1.8 L of 20 mM histadine in saline at pH 6.5 (minimally 1.5× concentrated volume). The resulting solution was concentrated to 14 mL (collecting final 2 mL of permeate solution for analysis). The pH was measured (pH 6.42), particle size (intensity and volume) was obtained (Z.Ave.=118.9) and the presence of targeting MMPi ligand confirmed by rphplc analysis as greater than 100 MMPi ligand molecules per liposome particle.

A sample (1.0 mL) was submitted for TD-1 assay, MMPi targeting assay, docetaxel area %, DSPC, Cholesterol, DSPE-PEG(2000) and Lyso-DSPC assay.

| Formulation | 10 mM Acetate in 300 mM Sucrose pH 5.5 |
| --- | --- |
| pH | 6.42 |
| Particle Size | 118.90 |
| Volume (mL) | 34.00 |
| Area %, TD-1 | 98.03 |
| %-BOC, RRT 0.41 | 0.00 |
| %-BOC, RRT 0.43 | 0.00 |
| %-ORO RRT 0.89 | 0.00 |
| %-ORO RRT 0.91 | 0.00 |
| %-ORO RRT 0.95 | 0.00 |
| %7-epi M3528, RRT 1.11 | 1.03 |
| % Docetaxel, RRT 1.44 | 0.95 |
| Prodrug, mg/ml | 3.34 |
| Target, ug/ml | 262.00 |
| Wt % Chol | 26.9 |
| Wt % DSPC | 58.3 |
| Wt % DSPE__PEG2000 | 9.6 |
| Wt % Lyso-DSPC | 5.2 |
| TD1/lipid | 0.157 |

Example 3

Preparation of MMP$^i$-Targeted Liposomal Oxaliplatin

Step 1

Figure 10:
FIG. 10 shows the synthesis of 1-benzyl 4-methyl 4-((4-phenoxyphenyl)sulfonyl)piperidine-1,4-dicarboxylate.

1-Benzyl 4-methyl 4-((4-phenoxyphenyl)sulfonyl)piperidine-1,4-dicarboxylate was synthesized as shown in FIG. 10. A 100 ml RBF equipped with magnetic stir bar was charged with 1.1 g (2.67 mmole) 4-methyl 4-((4-phenoxyphenyl)sulfonyl)piperidine-4-carboxylate 0.73 g (2.94 mmole) Cbz-OSu, 0.8 g (8.01 mmole) triethylamine. LCMS after 1 hour showed complete reaction with M+H=510 g/mol. The reaction was partitioned between EA and satd. aq. sodium bicarbonate. The organics were washed with 10 aq. KHSO$_4$, dried and concentrated to thick syrup that turned into white dry foam upon high vacuum drying. The product was dried overnight to afford 1.29 g (95% yield) of the Cbz ester that was used in Step 2.

Step 2

Figure 11:
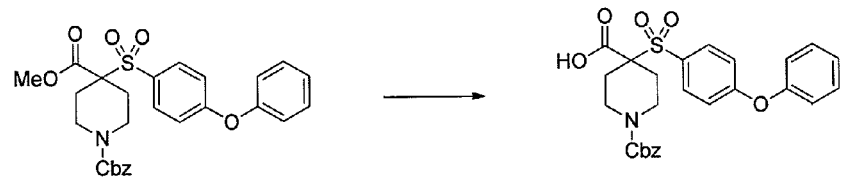
FIG. 11 shows the synthesis of 1-((benzyloxy)carbonyl)-4-((4-phenoxyphenyl)sulfonyl)piperidine-4-carboxylic acid.

1-((Benzyloxy)carbonyl)-4-((4-phenoxyphenyl)sulfonyl) piperidine-4-carboxylic acid was synthesized as shown in FIG. 11. A 250 ml RBF was charged with the 1.75 g of 1-benzyl 4-methyl 4-((4-phenoxyphenyl)sulfonyl)piperidine-1,4-dicarboxylate (3.39 mmole), 0.57 g (10.16 mmole) potassium hydroxide in 30 ml ethanol/7.5 ml water. The reaction mixture was stirred at 50° C. with LCMS monitoring. LCMS analysis indicated ~80% conversion after 1 hr and approximately 90% conversion after 2 hr with a trace of impurities appearing. The solution was concentrated to ¼ volume and partitioned between EA and 10% aq. Citric acid. The organics were washed with brine, dried, and concentrated in vacuo. The product was vacuum dried overnight to yield 1.6 g (95% yield) white solid that was used in Step 3.

Step 3

Figure 12:
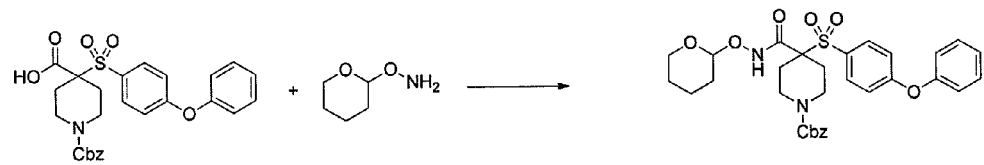
FIG. 12 shows the synthesis of benzyl 4-((4-phenoxyphenyl)sulfonyl)-4-(((tetrahydro-2H-pyran-2-yl)oxy)carbamoyl)piperidine-1-carboxylate.

Benzyl 4-((4-phenoxyphenyl)sulfonyl)-4-(((tetrahydro-2H-pyran-2-yl)oxy)carbamoyl)piperidine-1-carboxylate was synthesized as shown in FIG. 12. A 200 ml RBF equipped with magnetic stir bar was charged with 1.48 g (2.99 mmole) 1-((benzyloxy)carbonyl)-4-((4-phenoxyphenyl)sulfonyl)piperidine-4-carboxylic acid, 0.49 g (4.18 mmole) OTHP-hydroxylamine, 0.8 g (4.18 mmole) EDC, 0.64 g (4.18 mmole) HOBt, and 1.25 ml (8.96 mmole) triethylamine in 30 ml DMF. The reaction mixture was stirred at room temperature overnight. The reaction was concentrated in vacuo and partitioned between EA and satd. aq. sodium bicarbonate. The organics were washed with 10% aq. Citric acid, brine, dried, and concentrated in vacuo. This material was vacuum dried overnight to afford 1.50 g (85%) of dry white foam. The sample analyzed by direct infusion MS, which indicated >90% product with some trace impurities. HRMS$_{(theoretical)}$ M+H=595.2108 g/mol. HRMS$_{(observed)}$ M+H=595.2109 g/mol.

Step 4

Figure 13:
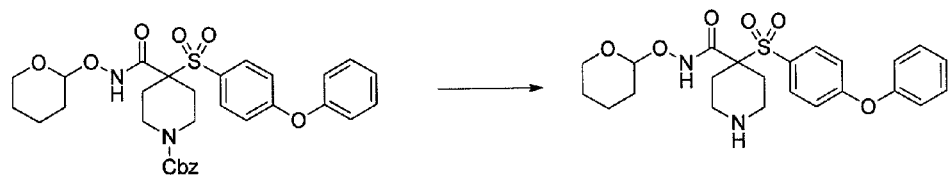
FIG. 13 shows the synthesis of 4-((4-phenoxyphenyl)sulfonyl)-4-(((tetrahydro-2H-pyran-2-yl)oxy)carbamoyl)piperidine.

4-((4-Phenoxyphenyl)sulfonyl)-4-(((tetrahydro-2H-pyran-2-yl)oxy)carbamoyl)piperidine was synthesized as shown in FIG. 13. A 200 ml RBF equipped with magnetic stir bar was charged with the 1.5 g of benzyl 4-((4-phenoxyphenyl)sulfonyl)-4-(((tetrahydro-2H-pyran-2-yl)oxy)carbamoyl)piperidine-1-carboxylate compound and 100 mg wet Degussa 5% Palladium on Carbon in 45 ml Methanol. The reaction mixture was purged with Argon for 5 minutes. Hydrogen was then bubbled over the solution for 1 hr. MS analysis (direct infusion) at this point indicated that the reaction was complete. The crude was filtered through Celite and the Celite was washed with 40 ml additional methanol. The methanol solution was concentrated in vacuo to 1.2 g white solid that was vacuum dried for 4 hours to yield 1.1 g product that was used in Step 5. HRMS$_{(observed)}$ M H=451.1737 g/mol.

Step 5

Figure 14:
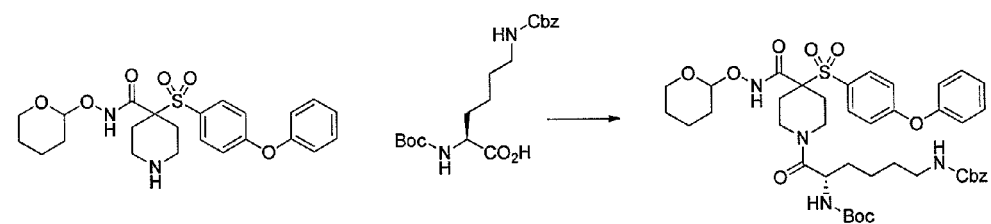
FIG. 14 shows the synthesis of benzyl tert-butyl ((5S)-6-oxo-6-(4-((4-phenoxyphenyl)sulfonyl)-4-(((tetrahydro-2H-pyran-2-yl)oxy)carbamoyl)piperidin-1-yl)hexane-1,5-diyl)dicarbamate.

Benzyl tert-butyl ((5S)-6-oxo-6-(4-((4-phenoxyphenyl)sulfonyl)-4-(((tetrahydro-2H-pyran-2-yl)oxy)carbamoyl)piperidin-1-yl)hexane-1,5-diyl)dicarbamate was synthesized as shown in FIG. 14. A 50 ml RBF equipped with magnetic stir bar was charged with 330 mg (0.72 mmole) 4-((4-phenoxyphenyl)sulfonyl)-4-(((tetrahydro-2H-pyran-2-yl)oxy) carbamoyl)piperidine, 286 mg (0.75 mmole) acid, 172 mg (0.9 mmole) EDC, 165 mg (1.1 mmole) HOBt, and 218 mg (2.15 mmole) triethylamine in 10 ml dry DMF. The reaction mixture was stirred at room temperature overnight. The DMF was removed and the reaction residue was partitioned between EA and satd. aq. sodium bicarbonate. The organics were washed with brine, dried, concentrated and vacuum dried to afford 585 mg (97% yield) crude white foam that was used in Step 7. HRMS$_{(theoretical)}$ M+Na=845.3402 g/mol. HRMS$_{(observed)}$ M+H=845.3406 g/mol.

Step 6

Figure 15:
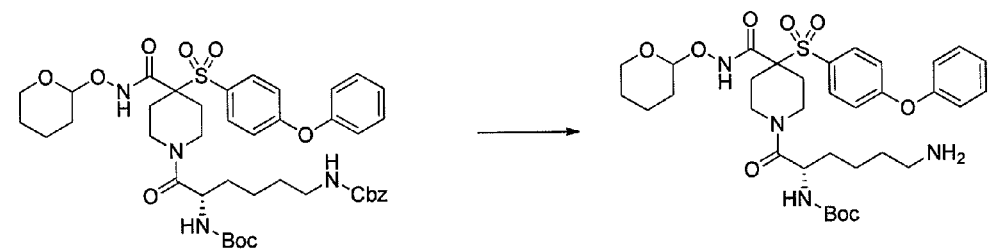
FIG. 15 shows the synthesis of tert-butyl ((2S)-6-amino-1-oxo-1-(4-((4-phenoxyphenyl)sulfonyl)-4-(((tetrahydro-2H-pyran-2-yl)oxy)carbamoyl)piperidin-1-yl)hexan-2-yl)carbamate.

Tert-butyl ((2S)-6-amino-1-oxo-1-(4-((4-phenoxyphenyl)sulfonyl)-4-(((tetrahydro-2H-pyran-2-yl)oxy)carbamoyl)piperidin-1-yl)hexan-2-yl)carbamate was synthesized as shown in FIG. 15. A 100 ml RBF was charged with 585 mg crude from Step 6, 88 mg 5% wet Palladium on Carbon (Degussa) in 45 ml Methanol. The reaction mixture was purged with Argon for ~5 minutes then hydrogen was slowly bubbled over the solution. LCMS analysis after 1 hour showed ~50-60% conversion to product with a M+H=689 g/mol. LCMS analysis after indicated about 75% conversion after three hours and about 90% conversion after four hours. The mixture was left to react for an additional hour. After a 5 minute Argon purge the reaction mixture was filtered through Celite. The reaction was concentrated and volatiles were chased 2× with dichloromethane and the white foam/solid was vacuum dried overnight to afford 492 mg (87%) white solid.

Step 7

Figure 16:
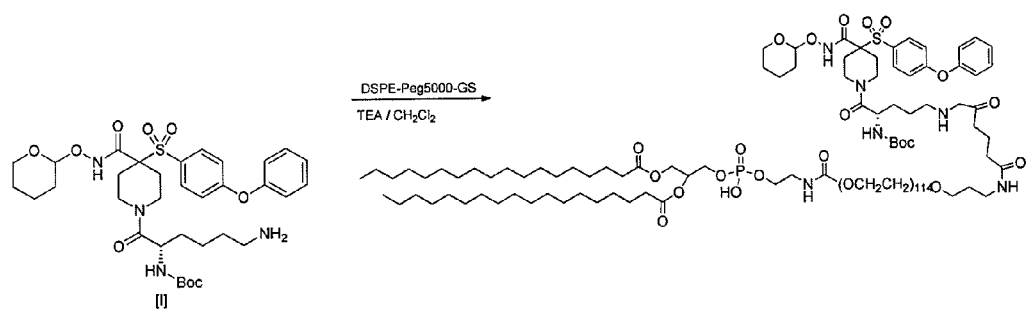
FIG. 16 shows the synthesis of a protected 4-((4-phenoxyphenyl)sulfonyl)-4-(((tetrahydro-2H-pyran-2-yl)oxy)carbamoyl)piperidine-PEG5000-DSPE conjugate.

A protected 4-((4-phenoxyphenyl)sulfonyl)-4-(((tetrahydro-2H-pyran-2-yl)oxy)carbamoyl)piperidine-PEG5000-DSPE conjugate was synthesized as shown in FIG. 16. A 25 ml RBF equipped with magnetic stir bar was charged with 200 mg DSPE-PEG5000-GS active ester (0.03 mmole), 19 mg (0.027 mmole) amine, and 12 mg (0.12 mmole) triethylamine. The reaction was stirred overnight under Argon. The product was concentrated and vacuum dried overnight. RPHPLC purification was done on a C8 column using 30 ml/min gradient of 20-100% over 13 minutes. The solvents were initially 20% 1:1 acetonitrile:isopropanol/80% 25 mM ammonium acetate in water with 5% acetonitrile. The product containing fractions were combined, concentrated to remove organic and the remainder was lyophilized to afford 93.5 mg (46% yield) white powder.

Step 8

Figure 17:
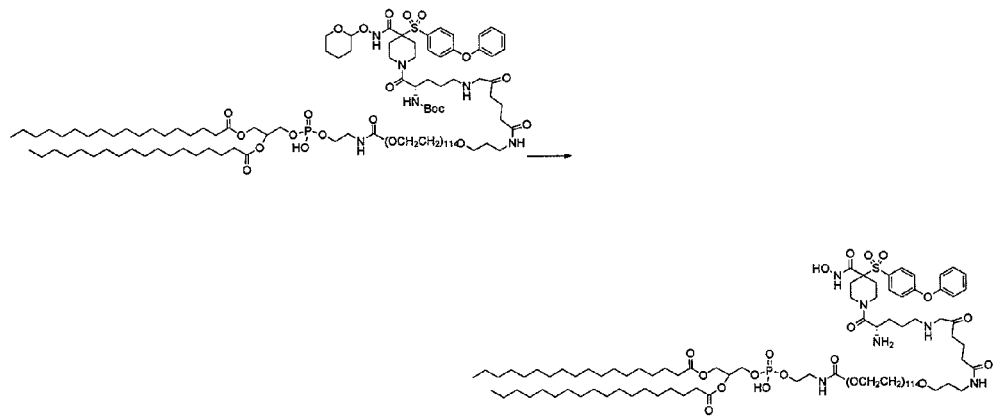
FIG. 17 shows the synthesis of an N-hydroxy-4-((4-phenoxyphenyl)-sulfonyl)piperidine-4-carboxamide-PEG5000-DSPE conjugate (Conjugate 2).
Figure 18:
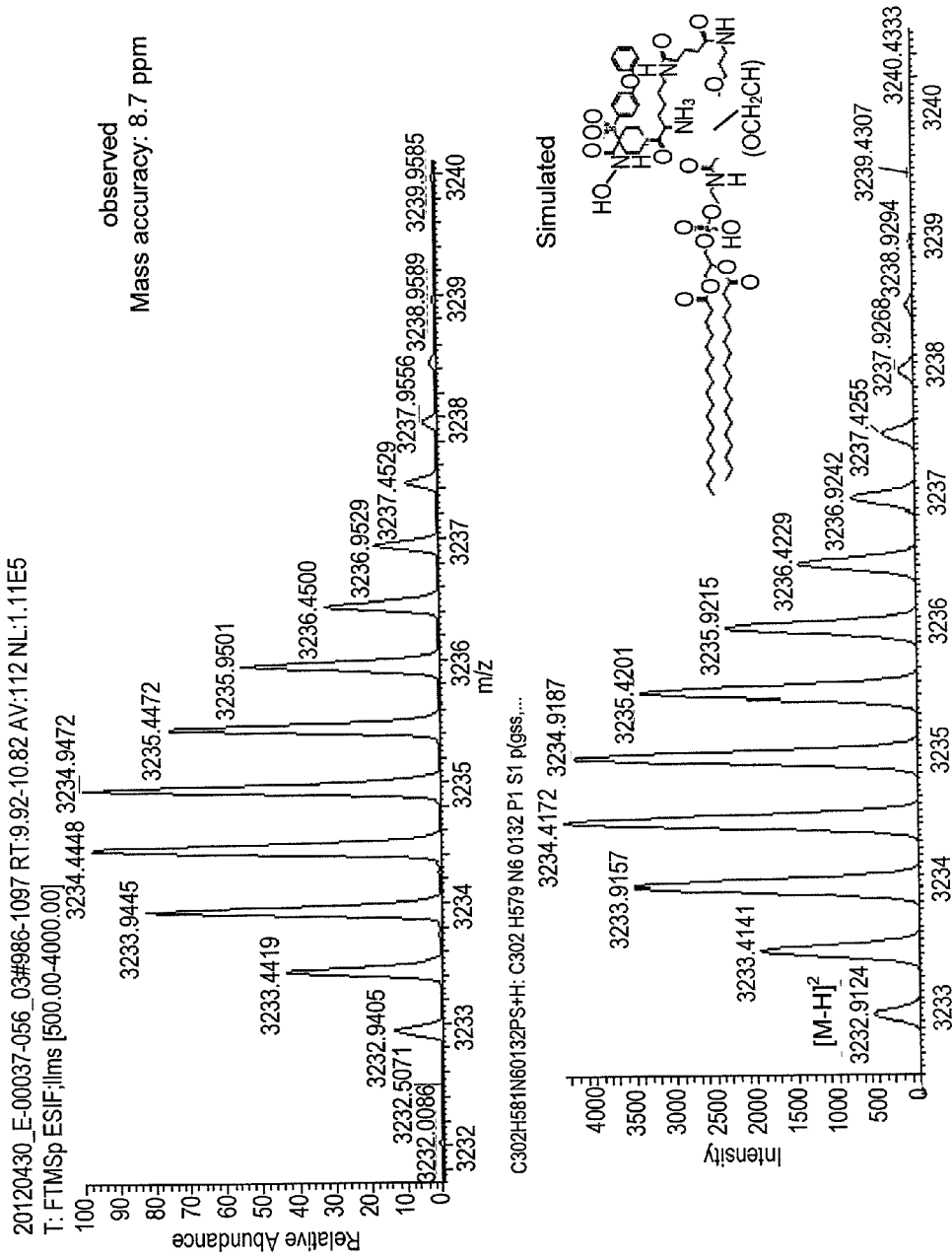
FIG. 18 shows mass spectra observed for Conjugate 2.

An N-hydroxy-4-((4-phenoxyphenyl)sulfonyl)piperidine-4-carboxamide-PEG5000-DSPE conjugate (Conjugate 2) was synthesized as shown in FIG. 17. A 100 ml RBF was charged with 93 mg in 1 ml TFA and 0.1 ml triethylsilane. The reaction was tumbled for 60 minutes. A sample was analyzed by LCMS, showing only desired formation of product. 10 ml water was added and aq. NH$_4$OH was used to bring the pH to 7.1. This was frozen and lyophilized overnight. To remove excess NH$_4$TFA, the crude was dissolved in 20 ml Millipore water and the solution was put it in a 3500 MW Pierce Slide-A-Lyzer cassette and stirred overnight in a 1 L beaker filled with Millipore water. The water was changed out twice more during the next 12 hours. The resulting aqueous dialyzed solution was frozen and lyophilized overnight to afford ~83 mgs of dry powder. A high resolution mass spectra for the product is shown in FIG. 18.

Preparation of Liposomes.

Conjugate 2 was dissolved in DI H$_2$O to generate either a 1.0 mg/mL or 2.0 mg/mL solution. It was then added to a phosphatidylcholine-based oxaliplatin-containing liposome preparation (at 1.0 mg/mL of liposome), and the resulting mixture was stirred at 37° C. for 8 h. The crude material was analyzed by SEC-HPLC. To remove free MMPi and free oxapliplatin, the crude formulation was passed through Spectrum Filter Module P/N: P-DI-500E-100-01N (prewashed with 1 L Millipore water) and washed with 900 mL (10-fold volume) of buffer (300 mM Sucrose with 20 mM sodium acetate, freshly prepared). This was typically accomplished over two days. Buffer and formulation were kept in the refrigerator overnight. The Spectrum Filter Module was rinsed with 0.1 N NaOH before storing overnight. After purification, the formulation was concentrated to a desired oxaliplatin concentration. The final sample was analyzed by SEC-HPLC. (10 uL of sample were diluted with 90 uL of PBS (1:9 dilution), and 5 uL were injected.) Particle size was measured on the Malvern Zetasizer. Lipids were analyzed via HPLC while Pt was quantified by ICP-MS. "Free" Pt was determined by ICP-MS of the filtrate obtained from 30 KDa Amicon centrifuge filters (9000 rpm for 10 min. at ambient temperature). The amount of targeting ligand inserted was determined by an HPLC method employing a calibration curve. Liposomes had an average particle size of 100 nm and included 54 ligands (Conjugate 2) per particle.

Example 4

Efficacy of MMPi-Liposomes in Nude Mice Bearing BxPC3 Xenograft Tumors

The MMP$^i$-targeted liposomal oxaliplatin prepared in Example 3 was administered to mice bearing BxPC3 pancreatic tumors.

FemaleHsd:Athymic Nude-Foxn1 nu/nu mice (($\approx$20 g) were implanted with ($2.5\times10^6$) BxPC3 cells subcutaneously into the right flank. Ten mice were used per dose group. The eight dose groups included saline, oxaliplatin, base oxaliplatin-containing liposomes at 22 mg/kg, 44 mg/kg, and 66 mg/kg, and the corresponding MMPi-liposomes at 31 mg/kg, 62 mg/kg, and 94 mg/kg.

Once tumors reached a median size of 150 mm$^3$, animals were randomized into groups, normalized by tumor volume among the groups. Animals without tumors were not included in this study. Test articles were dosed intravenously once.

Tumor length and width were measured with calipers 3 times per week and volume was calculated from the formula: Tumor Volume (mm$^3$)=Length*Width2*0.5. Animals were weighed once per week. Tumor volume was expressed as median and plotted as a function of time. Any animal removed from the study due to excess size beyond 2000 mm$^3$ had its value carried forward as 2000 mm$^3$ in subsequent plots. Tumor volume was also expressed as mean and plotted as a function of time (groups with less than 50% animals remaining were not be carried forward). Statistical significance of observed differences between growth curves was evaluated by One-Way ANOVA followed by posthoc test if significant.

Figure 19:
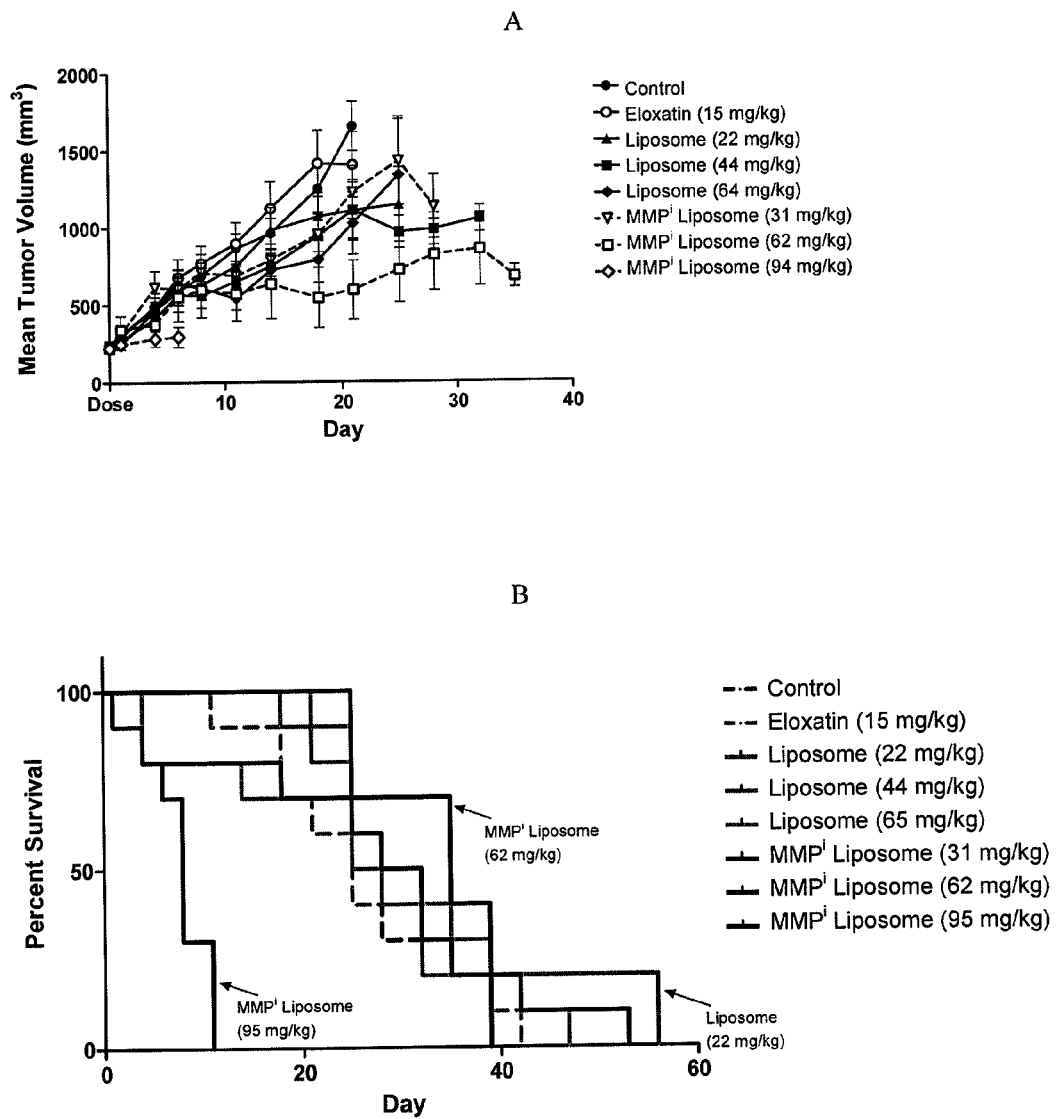
FIG. 19A shows mean tumor volume observed in mice bearing BxPC3 pancreatic tumors treated with MMP-targeted liposomal oxaliplatin, as compared to mice treated with untargeted liposomal oxaliplatin and non-liposomal oxaliplatin.
FIG. 19B shows percent survival rates for test groups treated with MMP-targeted liposomal oxaliplatin, untargeted liposomal oxaliplatin, and non-liposomal oxaliplatin.
Figure 20:
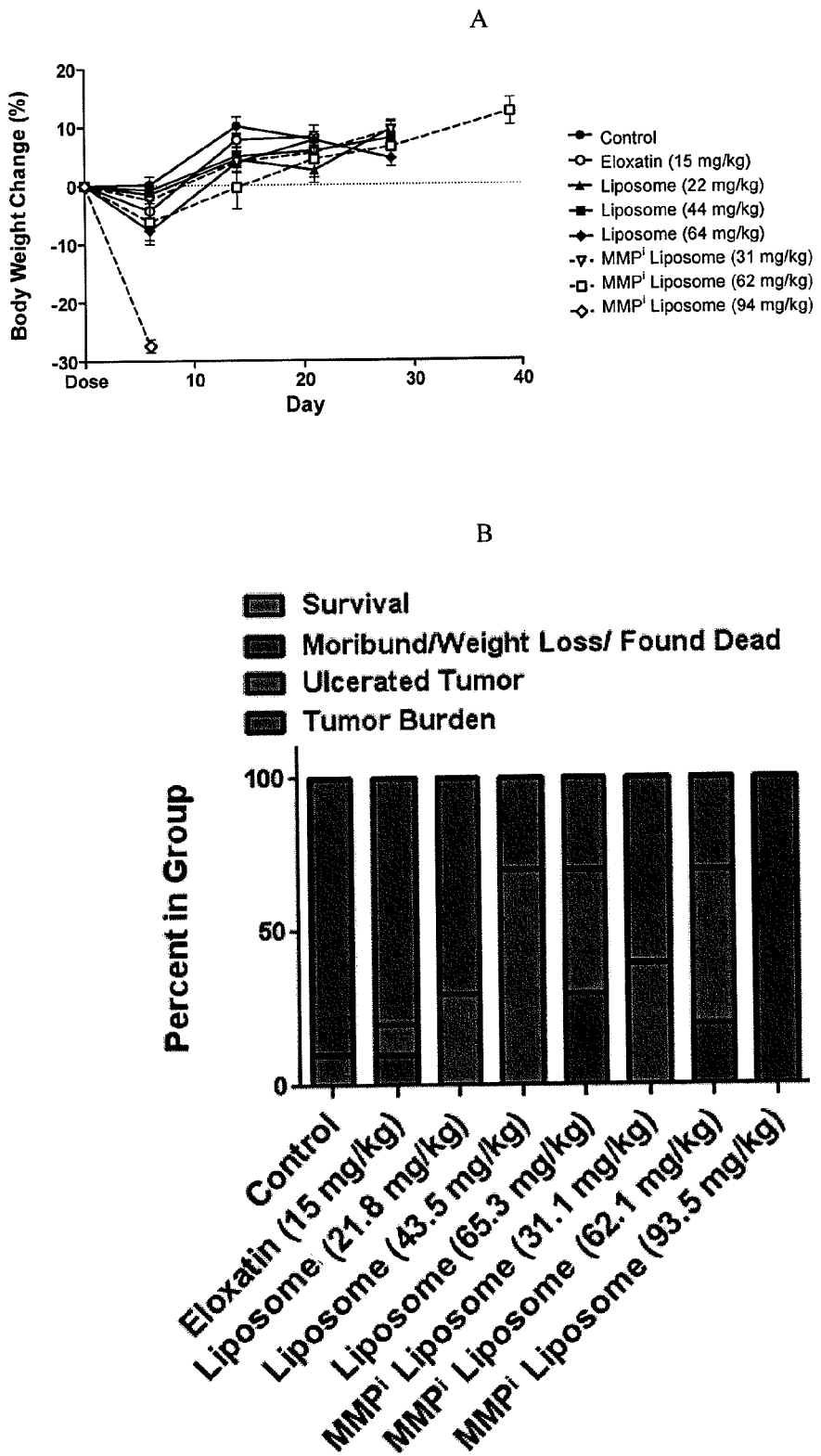
FIG. 20A shows the body weight changes observed in mice bearing BxPC3 pancreatic tumors treated with MMP-targeted liposomal oxaliplatin, as compared to mice treated with untargeted liposomal oxaliplatin and non-liposomal oxaliplatin.
FIG. 20B shows rates of survival, moribundity, weight loss, death, ulcerated tumors, and tumor burden for test groups treated with MMP-targeted liposomal oxaliplatin, untargeted liposomal oxaliplatin, and non-liposomal oxaliplatin.

Mean tumor volume and survival rates for mice treated with the targeted liposomes were compared to mean tumor volume and survival rates for control mice and mice that were administered untargeted oxaliplatin liposomes and Eloxatin (non-liposomal oxaliplatin). Administration of liposomal oxaliplatin led to lower tumor volumes than for Eloxatin, and administration of MMP$^i$-targeted liposomal oxaliplatin led to lower tumor volumes than for comparable doses of untargeted liposomal oxaliplatin (FIG. 19A. Mean tumor volume was measured after a single intravenous injection of test article. All doses are given as oxaliplatin molar equivalents. Values are mean±SEM for 5-10 mice/group.). FIG. 19B shows a Kaplan-Meier plot showing percent survival of mice bearing BxPC-3 human pancreatic xenografts after a single intravenous injection of MMP14 receptor targeting liposomes containing oxaliplatin (Targeted Liposome), non-targeted liposomes containing oxaliplatin, Eloxatin or saline. All doses are given as oxaliplatin molar equivalents. Each group started with 10 female mice bearing tumors. Significant differences in body weight change from the control group and the Eloxatin group were not observed for targeted and untargeted liposomes at most dosage levels (FIG. 20A; values are mean±SEM for 5-10 mice/group).

Example 5

Efficacy of MMPi-Liposomes in Nude Mice Bearing MMP14 Overexpressed HT-1080 Xenograft Tumors The MMP$^i$-targeted liposomal oxaliplatin prepared in Example 3 was administered to nude mice mice bearing humar fibrosarcoma HT1080 tumors over-expressing MMP14.

FemaleHsd:Athymic Nude-Foxn1 nu/nu mice (25 g) were implanted with ($5\times10^6$) HT1080/MMP14 tumor cells subcutaneously into the side. Ten mice were used per dose group. The six dose groups included saline, oxaliplatin, base oxaliplatin-containing liposomes at 15 mg/kg and 30 mg/kg, and the corresponding MMPi-liposomes at 15 mg/kg and 30 mg/kg.

Once tumors reached a median size of 150 mm$^3$, animals were randomized into groups, normalized by tumor volume among the groups. Animals without tumors were not included in this study. Test articles were dosed intravenously once.

Tumor length and width were measured with calipers 3 times per week and volume was calculated from the formula: Tumor Volume (mm$^3$)=Length*Width2*0.5. Animals were monitored and weighed twice per week. Tumor volume was expressed as median and plotted as a function of time. Any animal removed from the study due to excess size beyond 2000 mm$^3$ had its value carried forward as 2000 mm$^3$ in subsequent plots. Tumor volume was also expressed as mean and plotted as a function of time (groups with less than 50% animals remaining were not be carried forward). Statistical significance of observed differences between growth curves was evaluated by One-Way ANOVA followed by posthoc test if significant.

Figure 21:
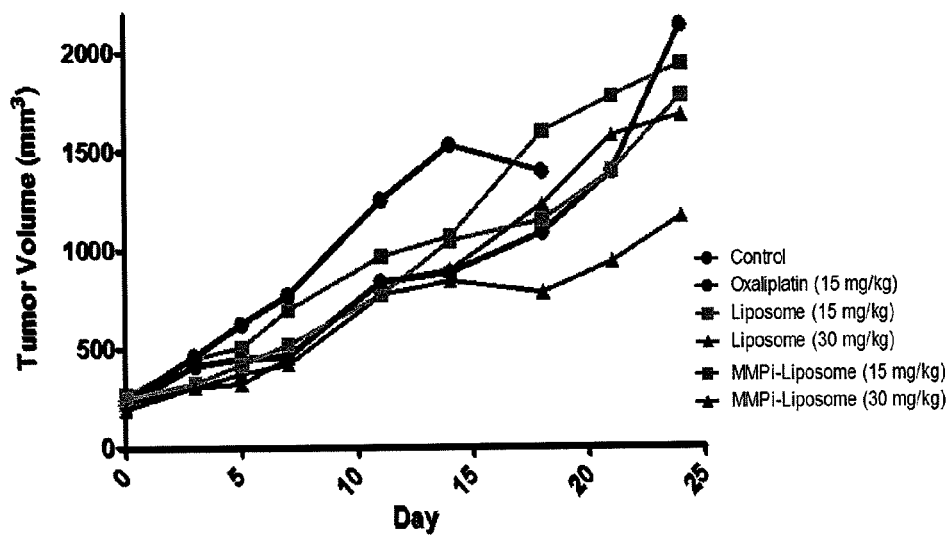
FIG. 21A shows mean tumor volume observed in nude mice bearing human fibrosarcoma HT1080 tumors overexpressing MMP14, treated with MMP-targeted liposomal oxaliplatin, as compared to mice treated with untargeted liposomal oxaliplatin and non-liposomal oxaliplatin.
FIG. 21B shows percent survival rates for test groups treated with MMP-targeted liposomal oxaliplatin, untargeted liposomal oxaliplatin, and non-liposomal oxaliplatin.
Figure 21:
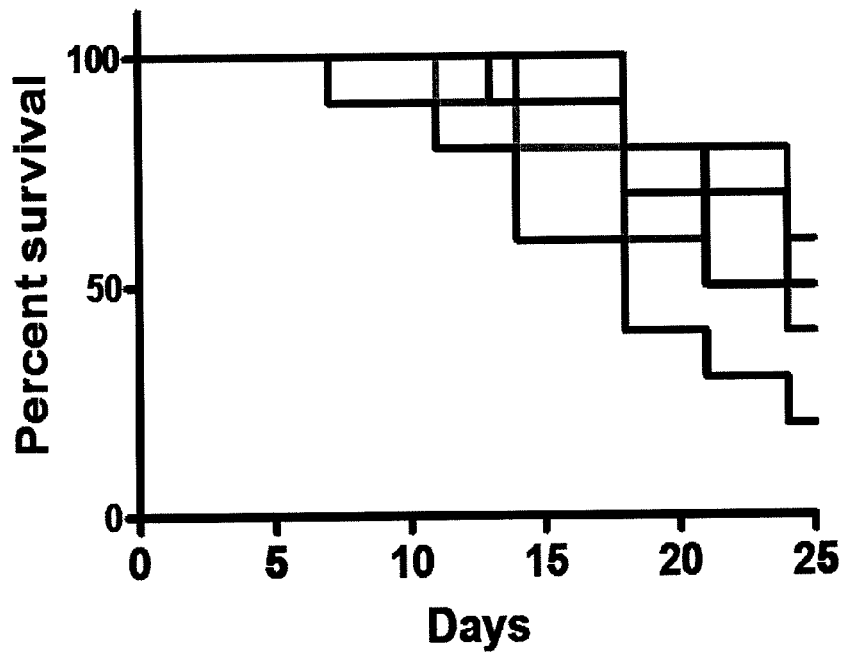

Mean tumor volume and survival rates for mice treated with the targeted liposomes were compared to mean tumor volume and survival rates for control mice and mice that were administered untargeted oxaliplatin liposomes and Eloxatin (non-liposomal oxaliplatin). Administration of liposomal oxaliplatin led to lower tumor volumes than for Eloxatin, and administration of MMP-targeted liposomal oxaliplatin at a dose of 30 mg/kg led to lower tumor volumes than for untargeted liposomal oxaliplatin at the same dose (FIG. 21A). Administration of MMP-targeted liposomal oxaliplatin at a dose of 30 mg/kg led to the highest percent survival of all test groups (FIG. 21B).

Example 6

MMP Inhibition by an MMP$^i$-Targeted Liposomal Formulation

The activity of MMP$^i$-targeted liposomal oxaliplatin sample prepared in Example 3 was tested against metalloproteinases MMP2 and MMP14.

rhMMP-2 (100 µg/mL) was activated by incubation with 1 mM APMA (p-aminophenylmercuric acetate) in assay buffer (50 mM Tris, 10 mM CaCl$_2$, 150 mM NaCl, 0.05% (v/v) Brij-35, pH 7.5) at 37° C. for 1 hr. The activated rhMMP-2 was diluted to 248 ng/mL in assay buffer. TAMP substrate (Mca-Lys-Pro-Leu-Gly-Leu-Dpa-Ala-Arg-NH$_2$) was diluted to 25 µM in assay buffer. 25 µL of 5× test samples containing the targeted liposomal formulation and 50 µL of 248 ng/mL activated rhMMP-2 were added to a 96 well black-sided plate. 50 µL of 25 µM substrate was added to start the enzymatic reactions, and fluorescence measurements ($\lambda_{ex}$=320 nm; $\lambda_{em}$=405 nm) were recorded in kinetic mode for 5 minutes.

rhMMP-14 (40 µg/mL) was activated by incubation with 0.86 µg/mL rhFurin in activation buffer (50 mM Tris, 1 mM CaCl$_2$, 0.05% (v/v) Brij-35, pH 9.0) at 37° C. for 1 hr. The activated rhMMP-14 was diluted to 1.24 µg/mL in assay buffer (50 mM Tris, 3 mM CaCl$_2$, 1 µM ZnCl$_2$, pH 8.5). MMP substrate (Mca-Lys-Pro-Leu-Gly-Leu-Dpa-Ala-Arg-NH$_2$) was diluted to 20 µM in assay buffer. 25 µL of 5× test samples containing the targeted liposomal formulation and 50 µL of 1.24 µg/mL activated rhMMP-14 were added to a 96 well black-sided plate. 50 µL of 20 µM substrate was added to start the enzymatic reactions, and fluorescence measurements ($\lambda_{ex}$=320 nm; $\lambda_{em}$=405 nm) were recorded in kinetic mode for 5 minutes.

Figure 22:
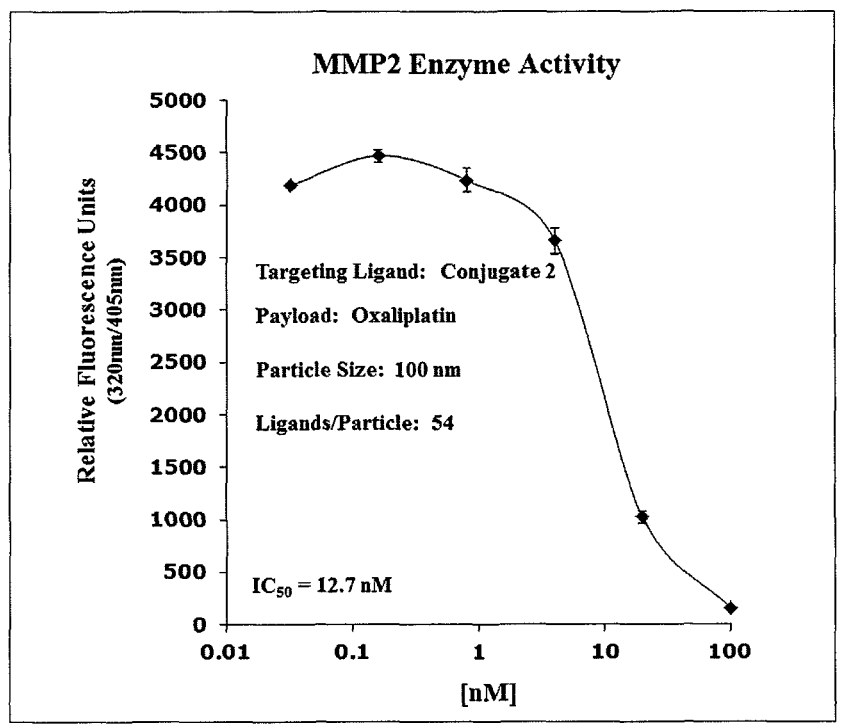
FIG. 22A shows the observed activity of MMP2 in the presence of MMP-targeted liposomal oxaliplatin at varying concentrations.
FIG. 22B shows the observed activity of MMP14 in the presence of MMP-targeted liposomal oxaliplatin at varying concentrations.
Figure 22:
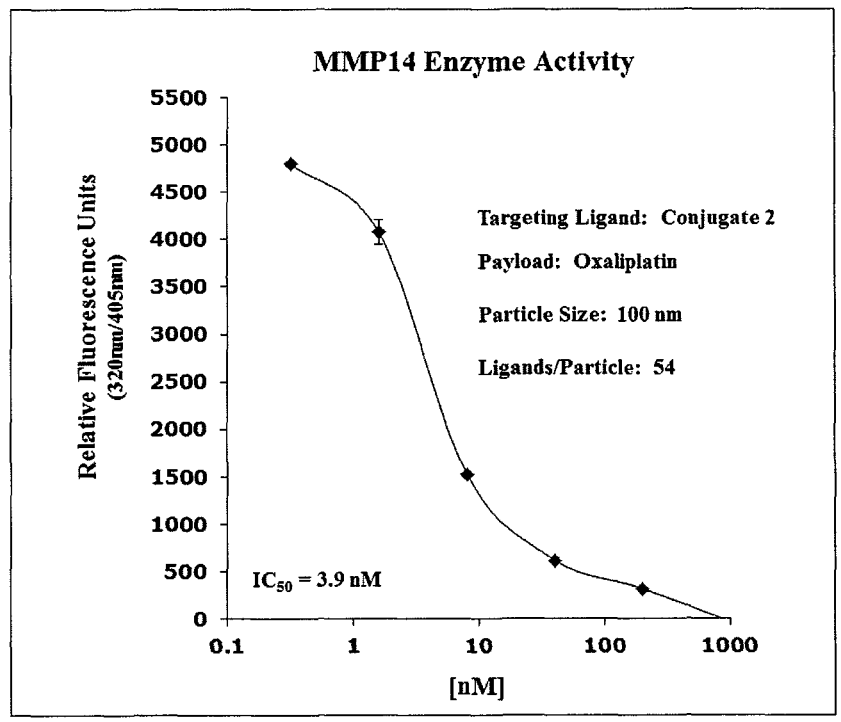

IC$_{50}$ values of 12.7 nm and 3.9 nm were observed for MMP2 and MMP14, respectively (FIG. 22A and FIG. 22B).

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A targeted delivery composition, comprising:
   (a) a nanocarrier including a therapeutic or diagnostic agent or a combination thereof; and
   (b) a conjugate having the formula:

A-(LPEG)-MMP$^i$;

wherein,
   A is an attachment component for attaching said conjugate to said nanocarrier;
   (LPEG) is selected from:
   (i) a linking group having a linear assembly of from 1 to 3 polyethylene glycol components,
   (ii) a linking group having the formula [(EG)(P)]$_m$ wherein each EG is an ethylene glycol group independently selected from the group consisting of triethylene glycol, tetraethylene glycol, pentaethylene glycol, hexaethylene glycol, heptaethylene glycol and octaethylene glycol, P is a phosphoryl or thiophosphoryl group, and m is an integer of from 1 to 20; or
   (iii) a linking group having the formula —Z$^1$—Z$^2$—Z$^3$—, wherein
   Z$^1$ and Z$^3$ are independently selected from the group consisting of a PEG component having a defined length and W$_n$, wherein W is an amino acid and the subscript n is an integer from 0 to 3; and
   Z$^2$ is selected from the group consisting of a PEG component having a defined length and a coupling group selected from an amide, thioamide, ester, carbamate or urea for connecting Z$^1$ and Z$^3$; and MMP$^i$ is a MMP enzyme inhibitor having the formula:

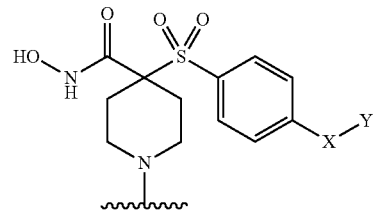

wherein
X is a member selected from the group consisting of O and S;
Y is a member selected from the group consisting of pyridyl and phenyl, wherein said phenyl is optionally substituted with OH, OCH$_3$, OCF$_3$ and CH$_3$; and
the wavy line indicates the point of attachment to (LPEG).

2. The targeted delivery composition of claim 1, wherein (LPEG) is —Z$^1$—Z$^2$—Z$^3$—.

3. The targeted delivery composition of claim 2, wherein Z$^1$ is W$_n$; Z$^2$ is selected from an amide, thioamide, ester, carbamate or urea; and Z$^3$ is a PEG component having a defined length.

4. The targeted delivery composition of claim 3, wherein the subscript n is 3.

5. The targeted delivery composition of claim 3, wherein the subscript n is 2.

6. The targeted delivery composition of claim 3, wherein the subscript n is 1.

7. The targeted delivery composition of claim 1, wherein the subscript n is 0.

8. The targeted delivery composition of claim 1, wherein the amino acid is an α-amino acid.

9. The targeted delivery composition of claim 8, wherein the α-amino acid is selected from the group consisting of aspartic acid, glutamic acid, lysine, arginine, and glycine.

10. The targeted delivery composition of claim 9, wherein the α-amino acid is selected from the group consisting of glutamic acid and lysine.

11. The targeted delivery composition of claim 1, wherein said nanocarrier is selected from the group consisting of a liposome, a micelle, a lipid-coated bubble, and a block copolymer micelle.

12. The targeted delivery composition of claim 1, wherein said nanocarrier further comprises a stealth agent.

13. The targeted delivery composition of claim 1, wherein said nanocarrier comprises a therapeutic agent selected from the group consisting of doxorubicin, cisplatin, oxaliplatin, carboplatin, 5-fluorouracil, gemcitibine and a taxane.

14. The targeted delivery composition of claim 1, wherein said attachment component is a lipid.

15. The targeted delivery composition of claim 1, wherein (LPEG) has the formula:

—Z$^1$—Z$^2$—Z$^3$— wherein each of Z$^1$ and Z$^3$ are a PEG component having a defined length, and Z$^2$ is a coupling group selected from an amide, thioamide, ester, carbamate or urea for connecting the two PEG components.

16. The targeted delivery composition of claim 1, wherein MMP$^i$ is selected from the group consisting of

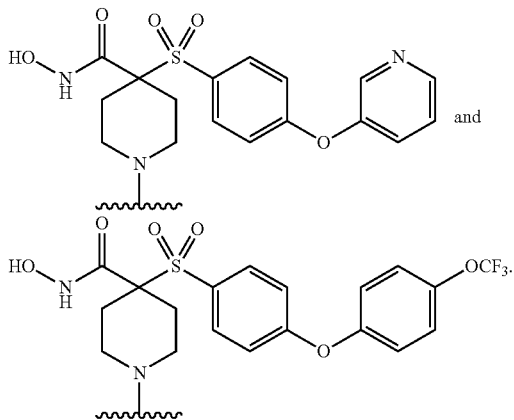

and

17. The targeted delivery composition of claim 1, wherein MMP$^i$ is selected from the group consisting of

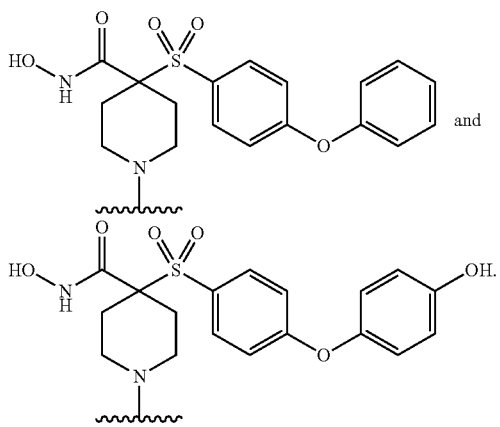

and

18. A targeted delivery composition, comprising:
(a) a nanocarrier including a therapeutic or diagnostic agent or a combination thereof; and
(b) a conjugate having the formula:

A-(LPEG)-MMP$^i$;

wherein,
A is an attachment component for attaching said conjugate to said nanocarrier;
(LPEG) is a linking group having a linear assembly of from 1 to 3 polyethylene glycol components, or a linking group having the formula [(EG)(P)]$_m$ wherein each EG is an ethylene glycol group independently selected from the group consisting of triethylene glycol, tetraethylene glycol, pentaethylene glycol, hexaethylene glycol, heptaethylene glycol and octaethylene glycol, P is a phosphoryl or thiophosphoryl group, and m is an integer of from 1 to 20; and
MMP$^i$ is a MMP enzyme inhibitor.

19. The targeted delivery composition of claim 18, wherein said MMP inhibitor has the formula:

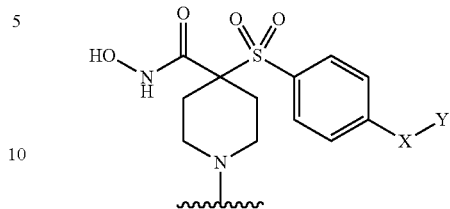

wherein
X is a member selected from the group consisting of O and S;
Y is a member selected from the group consisting of pyridyl and phenyl, wherein said phenyl is optionally substituted with OH, OCH$_3$, OCF$_3$ and CH$_3$; and
the wavy line indicates the point of attachment to (LPEG).

20. The targeted delivery composition of claim 18, wherein said nanocarrier is selected from the group consisting of a liposome, a micelle, a lipid-coated bubble, and a block copolymer micelle.

21. The targeted delivery composition of claim 18, wherein said nanocarrier further comprises a stealth agent.

22. The targeted delivery composition of claim 21, wherein said stealth agent is poly(ethylene glycol).

23. The targeted delivery composition of claim 18, wherein said therapeutic or diagnostic agent is embedded in, encapsulated in, or tethered to said nanocarrier.

24. The targeted delivery composition of claim 23, wherein said nanocarrier is a liposome.

25. The targeted delivery composition of claim 18, wherein said nanocarrier is a liposome selected from the group consisting of SUVs, LUVs and MLVs.

26. The targeted delivery composition of claim 18, wherein said nanocarrier comprises a therapeutic agent selected from the group consisting of doxorubicin, cisplatin, oxaliplatin, carboplatin, 5-fluorouracil, gemcitibine and a taxane.

27. The targeted delivery composition of claim 18, wherein said diagnostic agent is a radioactive agent, a fluorescent agent, or a contrast agent.

28. The targeted delivery composition of claim 18, wherein said diagnostic agent is a radioactive agent selected from the group consisting of $^{111}$In-DTPA, $^{99m}$Tc(CO)$_3$-DTPA, and $^{99m}$Tc(CO)$_3$-ENPy2.

29. The targeted delivery composition of claim 18, wherein said diagnostic agent is a fluorescent agent.

30. The targeted delivery composition of claim 18, wherein said diagnostic agent is a MR agent or a X-ray contrast agent.

31. The targeted delivery composition of claim 18, wherein said attachment component comprises a functional group for covalent attachment to said nanocarrier.

32. The targeted delivery composition of claim 18, wherein said attachment component is a lipid.

33. The targeted delivery composition of claim 32, wherein said lipid is a phospholipid, glycolipid, sphingolipid, or cholesterol.

34. The targeted delivery composition of claim 18, wherein the A portion of said conjugate is present in a lipid bilayer portion of said nanocarrier.

35. The targeted delivery composition of claim 34, wherein said nanocarrier is a liposome.

\* \* \* \* \*